US011726076B2

(12) United States Patent
Davis et al.

(10) Patent No.: US 11,726,076 B2
(45) Date of Patent: Aug. 15, 2023

(54) TECHNIQUES FOR MONITORING SLUMP CHARACTERISTIC OF CONCRETE IN A ROTATING CONTAINER OR DRUM

(71) Applicant: CiDRA CORPORATE SERVICES LLC, Wallingford, CT (US)

(72) Inventors: Michael A. Davis, Glastonbury, CT (US); Douglas H. Loose, Southington, CT (US); David Vincent Newton, Madison, CT (US); Charles Winston, Glastonbury, CT (US); Alan D. Kersey, South Glastonbury, CT (US)

(73) Assignee: CIDRA CONCRETE SYSTEMS INC., Wallingford, CT (US)

( * ) Notice: Subject to any disclaimer, the term of this patent is extended or adjusted under 35 U.S.C. 154(b) by 651 days.

(21) Appl. No.: 16/638,237

(22) PCT Filed: Aug. 22, 2018

(86) PCT No.: PCT/US2018/047479
§ 371 (c)(1),
(2) Date: Feb. 11, 2020

(87) PCT Pub. No.: WO2019/040595
PCT Pub. Date: Feb. 28, 2019

(65) Prior Publication Data
US 2020/0217833 A1    Jul. 9, 2020

Related U.S. Application Data

(60) Provisional application No. 62/548,727, filed on Aug. 22, 2017, provisional application No. 62/548,699, (Continued)

(51) Int. Cl.
*G01N 33/38* (2006.01)
*B28C 5/42* (2006.01)
(Continued)

(52) U.S. Cl.
CPC ......... *G01N 33/383* (2013.01); *B28C 5/422* (2013.01); *B28C 7/024* (2013.01); *G01N 11/14* (2013.01);
(Continued)

(58) Field of Classification Search
None
See application file for complete search history.

(56) References Cited

U.S. PATENT DOCUMENTS

| 3,731,909 A | 5/1973 | Johnson |
| 4,008,093 A | 2/1977 | Kitsuda et al. |

(Continued)

FOREIGN PATENT DOCUMENTS

| GB | 2392502 A | * 3/2004 | ............... B60P 3/16 |
| WO | 2013188620 A2 | 12/2013 | |

OTHER PUBLICATIONS

RussTech. (n.d.). Factors which may influence air content—russtech. Factors which may influence air content. Retrieved Nov. 16, 2022, from https://www.russtechnet.com/uploads/product-notes/factors-which-may-influence-air-content.pdf (Year: 2022).*

(Continued)

*Primary Examiner* — Alexander A Mercado
(74) *Attorney, Agent, or Firm* — Ware, Fressola, Maguire & Barber LLP

(57) ABSTRACT

A system features an acoustic sensor configured to mount on a wall of a mixing drum, sense an acoustic characteristic of a mixture of a slurry, including concrete, contained in a mixing drum when rotating, and provide acoustic sensor signaling containing information about the acoustic characteristic sensed; and a signal processor configured to receive the acoustic sensor signaling, and determine corresponding signaling containing information about a slump character- (Continued)

istic of the mixture of concrete contained in the mixing drum, based upon the signaling received.

5 Claims, 19 Drawing Sheets

Related U.S. Application Data filed on Aug. 22, 2017, provisional application No. 62/548,712, filed on Aug. 22, 2017.

(51) Int. Cl.
*B28C 7/02* (2006.01)
*G01N 11/14* (2006.01)
*G01N 29/14* (2006.01)
*G01N 11/00* (2006.01)

(52) U.S. Cl.
CPC ...... *G01N 29/14* (2013.01); *G01N 2011/0046* (2013.01); *G01N 2291/106* (2013.01)

(56) References Cited

U.S. PATENT DOCUMENTS

| | | | |
|---|---|---|---|
| 4,560,737 A | 12/1985 | Yamamoto et al. | |
| 5,713,663 A | 2/1998 | Zandberg et al. | |
| 5,951,908 A | 9/1999 | Cui et al. | |
| 6,484,079 B2 | 11/2002 | Buckelew et al. | |
| 8,020,431 B2 | 9/2011 | Cooley et al. | |
| 8,858,061 B2 | 10/2014 | Berman | |
| 9,199,391 B2 | 12/2015 | Beaupre et al. | |
| 9,939,420 B2* | 4/2018 | Bellotti | G01N 29/348 |
| 11,275,009 B2* | 3/2022 | Biesak | G01N 11/14 |
| 11,275,056 B2* | 3/2022 | Biesak | G01N 29/024 |
| 2007/0144240 A1 | 6/2007 | Andle | |
| 2009/0171595 A1 | 7/2009 | Bonilla Benegas | |
| 2013/0192351 A1 | 8/2013 | Fernald et al. | |
| 2014/0297204 A1* | 10/2014 | Biesak | G01N 29/42 |
| | | | 702/56 |
| 2015/0082862 A1 | 3/2015 | Loose et al. | |
| 2015/0135801 A1* | 5/2015 | Davis | G01N 29/00 |
| | | | 73/19.08 |
| 2017/0217047 A1* | 8/2017 | Leon | B28C 5/4231 |
| 2017/0370898 A1* | 12/2017 | Radjy | G01N 33/38 |
| 2018/0052146 A1* | 2/2018 | Radjy | G01N 33/383 |
| 2019/0204197 A1* | 7/2019 | Beaupre | G01N 29/4427 |
| 2020/0124570 A1* | 4/2020 | Biesak | G01F 1/74 |
| 2020/0171704 A1* | 6/2020 | Davis | G01N 33/383 |
| 2020/0173899 A1* | 6/2020 | Biesak | G01N 33/383 |
| 2020/0217833 A1* | 7/2020 | Davis | G01N 29/245 |
| 2022/0178806 A1* | 6/2022 | Biesak | G01N 33/383 |

OTHER PUBLICATIONS

International Search Report issued in International Patent Application PCT/US18/47479 dated Jan. 7, 2019.

Nathan Tregger, et al; "Introducing a New Sensor for In-Mixer Air Volume Measurement" Proceedings of 2013 PCI Convention; 2013; pp. 1-16.

* cited by examiner

SECTION A-A

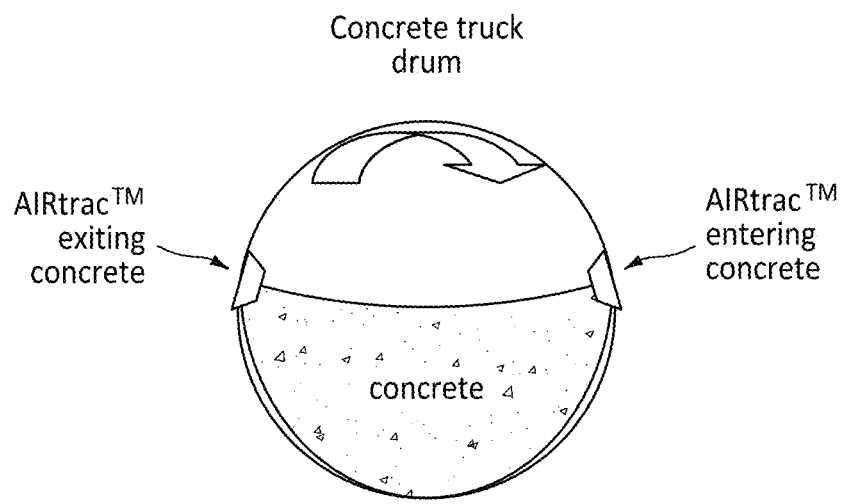
FIG. 4
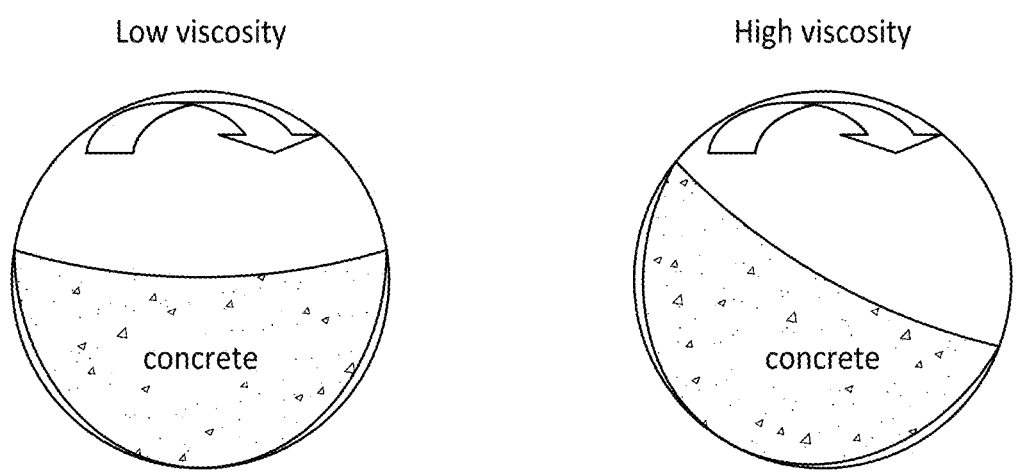
FIG. 5A
FIG. 5B

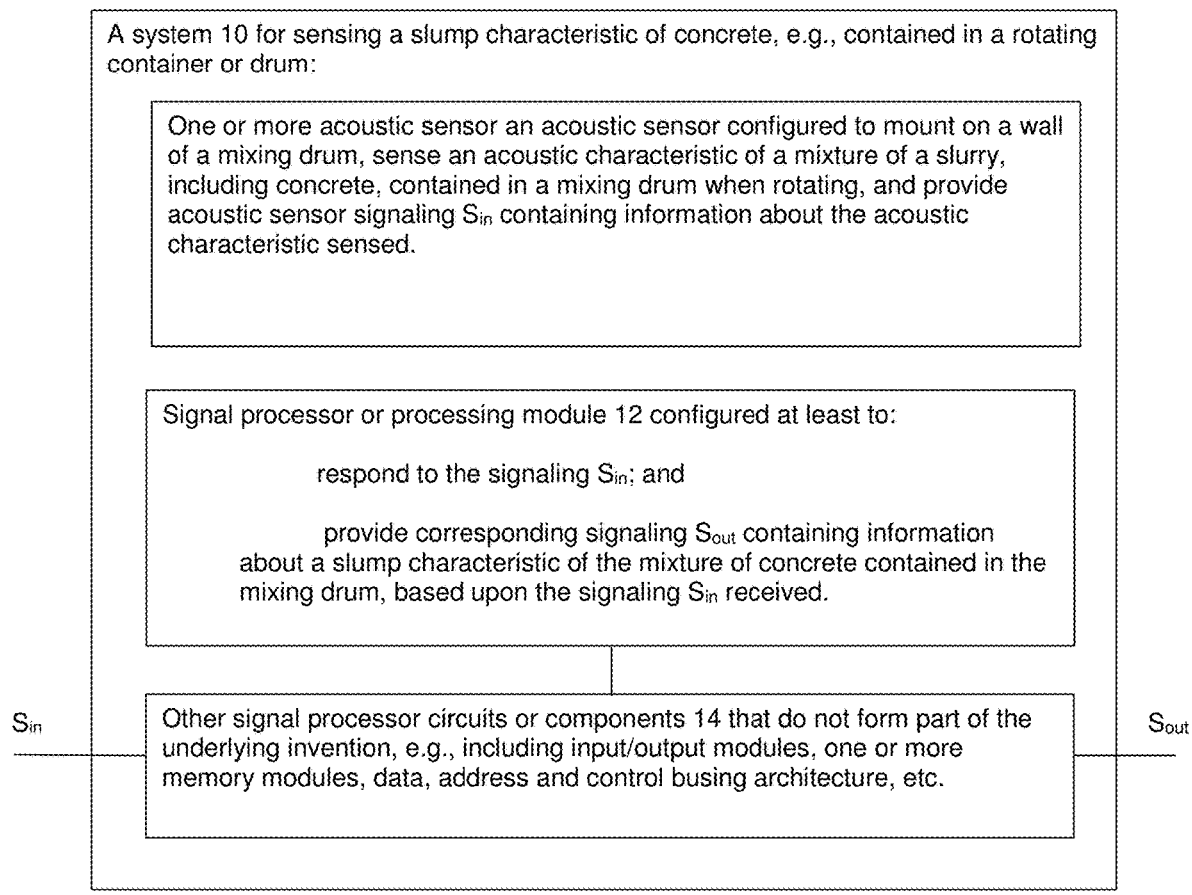
Figure 20: The System

TECHNIQUES FOR MONITORING SLUMP CHARACTERISTIC OF CONCRETE IN A ROTATING CONTAINER OR DRUM

CROSS-REFERENCE TO RELATED APPLICATIONS

This application claims benefit to provisional patent application Ser. No. 62/548,699 (712-2.452//CCS-0178), 62/548,712 (712-2.453//CCS-0183), 62/548,727 (712-2.454//CCS-0185), all filed on 22 Aug. 2017, which are all hereby incorporated by reference in their entirety.

This application is related to patent application Ser. No. 14/350,711 (712-2.365-1-1), filed 9 Apr. 2014, which corresponds to PCT/US2012/060822, filed 18 Oct. 2012, claiming benefit to provisional patent application serial nos. 61/548,549 and Ser. No. 61/548,563, both filed 18 Oct. 2011; which are all incorporated by reference in their entirety.

The aforementioned applications were all assigned to the assignee of the present application, which builds on this family of technology.

BACKGROUND OF THE INVENTION

1. Field of Invention

This invention relates to a technique for sensing parameters of concrete in a rotating container or drum, e.g., including a slump characteristic.

2. Description of Related Art

The measurement of concrete slump in readymix delivery is an important quality parameter that both the supplier and the customer need to know at the point of delivery. This is done most often manually using a cone-shaped instrument, known as an Abram's cone. Recently, there has been growing interest in the real-time measurement of another crucial parameter—entrained air in both central mixers for prefabricated concrete, and readymix deliveries.

Several patents have described systems for the use of automated methods for providing a measure of the slump in a concrete delivery truck. These include the use of methods to monitor the power/torque or hydraulic pressure required to drive the drum (U.S. Pat. Nos. 3,731,909, 4,008,093, 5,713,663, 8,020,431 (see references labeled [1]-[4] below), the use of a probe internal to the drum for measuring the resistance to flow in the concrete slurry (U.S. Pat. No. 8,858,061, U.S. Pat. No. 199,391 (see references labeled [5] and [6] below) and an approach based on the determination of the slurry surface angle relative to the horizontal plane in a rotating drum mixer, as determined via the as termed 'banking angle' in US patent publication no. US 2009/0171595 (see reference labeled [7] below). Approaches to remotely monitor and communicate the concrete status in real-time have also been described, as in U.S. Pat. No. 6,484,079 (see references labeled [8] below).

The assignee of the present invention has developed a means of measuring entrained air in wet concrete, which is disclosed in the aforementioned patent application Ser. No. 14/350,711 (712-2.365-1-1). The measurement device or acoustic probe is called, or known in the industry as, AIRtrac™ or AIRtrac Mobile™. The AIRtrac™ sensor may be permanently installed on a rotating container/concrete mixer drum or on the hatch door of a concrete mixer drum.

Consistent with that disclosed in the aforementioned patent application Ser. No. 14/350,711 (712-2.365-1-1), and by way of example, FIGS. 1a to 1e show the AIRtrac™ sensor, that is generally indicated as 100 and may include an acoustic-based air probe like element 101. The acoustic-based air probe 101 may include an acoustic source generally indicated as 102 (see FIG. 1d) configured to provide an acoustic signal into a mixture of concrete; and an acoustic receiver generally indicated as 104 (see FIG. 1e) configured to be substantially co-planar with the acoustic source 102, to respond to the acoustic signal, and to provide signaling containing information about the acoustic signal injected into the mixture of concrete. By way of example, the acoustic source 102 may consist of an arrangement of parts and components and is best shown in detail in FIG. 1d. By way of example, the acoustic receiver 104 may consist of at least an arrangement of one or more transducers and fills and is best shown in FIG. 1e.

The acoustic-based air probe 101 may include a planar probing surface 106 having a first aperture 106a formed therein configured to receive part of the acoustic source 102, including a hardened steel piston 122, as best shown in FIG. 1d. At the interface with the planar probing surface 106, the hardened steel piston 122 is surrounded by a circumferential channel 122a, so as not to be in physical contact with the planar probing surface 106. The planar probing surface 106 may include at least one second aperture 106b, 106c formed therein configured to receive at least one part 104', 104" of the acoustic receiver 104. The part 104', 104" are shown as a protective polyurethane rubber member in FIG. 1e. The planar probing surface 106 may be configured as a hardened steel face plate, although the scope of the invention is intended to include using other type or kinds of materials either now known or later developed in the future. The acoustic receivers 104 are configured in relation to the center of the hardened steel piston 122 of the acoustic source 102 and defined by a radius R, as best shown in FIG. 1c, so that the acoustic receivers 104 are arranged and configured substantially on the circumference of a circle defined by the radius R from the center of the hardened steel piston 122.

The acoustic receiver 104 may include, or take the form of, a dynamic pressure transducer, as best shown in FIG. 1e.

In operation, and by way of example, the acoustic receiver 104 may be configured to receive acoustic signals, e.g., having a frequency in a range of about 100-500 Hz, including 330 Hz, although the scope of the invention is intended to include using other frequencies and other ranges either now known or later developed in the future.

By way of example, the acoustic source 102 may include, or take the form of, or be configured as, a floating mass, consistent with that shown in FIG. 1d.

In FIG. 1d, the acoustic source 102 is shown in the form of a piston module assembly 120 having the rigid hardened steel piston 122 configured with a channel 124 to receive, or be coupled to, a piston shaft 126. The acoustic-based air probe 101 has a base plate disk 125 that contains the piston module assembly 120, as well as other components in FIG. 1d. The rigid hardened steel piston 122 is enclosed, surrounded and configured to move in relation to a low durometer cast silicone rubber 123 and photo-etched flexures 127, so as to provide the floating mass aspect of the acoustic source 102. The low durometer cast silcone rubber 123 may also be configured to perform sealing functionality in relation to the mixture of the concrete. The acoustic source 102 may also include a vibration isolated actuator block assembly 128, best identified in FIG. 1b, having a stationary voice coil actuator field assembly 130 in combination with a voice coil actuator field assembly 132 having an accelerometer transducer configuration. The vibration isolated actuator block assembly 128 may be configured to drive and vibrate the piston shaft 126, consistent with that shown in FIG. 1d, so as to provide the acoustic signal to the mixture of the concrete when the acoustic-based air probe is inserted into the mixture. The apparatus 100 may also be configured with signal processing technology (not shown) for driving the acoustic source 102, as would be appreciated by a person skilled in the art.

The acoustic-based air probe 101 may include a fluid/media temperature sensor 134, consistent with that shown in FIG. 1d, configured to provide a temperature reading of the mixture.

The acoustic-based air probe 101 may include a voice coil temperature sensor 136, consistent with that shown in FIG. 1d, configured to provide a temperature reading of the stationary voice coil actuator field assembly 130.

The acoustic-based air probe 101 may include two acoustic receivers 104, 104', that may take the form of the two dynamic pressure transducers, consistent with that shown in FIG. 1e.

The acoustic-based air probe 101 may include some combination of a connector/wiring cover plate 140, and various connectors configured in relation to the same, including a pressure sensor no. 1 connector 142 for providing the signaling in relation to one pressure sensor, a pressure sensor no. 2 connector 144 for providing the signaling in relation to the other pressure sensor, a voice coil drive connector 146 for providing the signaling in relation to the voice coil drive 130 (FIG. 1d), a temperature sensor connector 148 for providing the signaling in relation to a temperature, and an accelerometer connector 150 for providing the signaling in relation to the voice coil actuator moving coil assembly 132 (FIG. 1d), all shown in FIG. 1b.

SUMMARY OF THE INVENTION

In its broadest sense, the present invention provides a new and unique system for determining a slump characteristic having an acoustic sensor and a signal processor.

The acoustic sensor may be configured to mount on a wall of a mixing drum, sense an acoustic characteristic of a mixture of a slurry, including concrete, contained in a mixing drum when rotating, and provide acoustic sensor signaling containing information about the acoustic characteristic sensed.

The signal processor may be configured to
receive the acoustic sensor signaling, and
determine corresponding signaling containing information about a slump characteristic of the mixture of concrete contained in the mixing drum, based upon the signaling received.

The system may include one or more of the following features:

The acoustic sensor may include PVDF patches or PZT elements.

The PVDF patches or PZT elements may be mounted on an exterior mixing drum wall of the mixing drum.

The PVDF patches or PZT elements may be covered by an outer protective housing/cover, including where the outer protective housing/cover provides external noise protection.

The signal processor may be configured to determine the slump characteristic based upon noise characteristics at different spatial locations that indicate differences in the slump of the mixture of concrete.

The acoustic sensor may be configured to sense a first acoustic characteristic when the concrete is lifted by a vane of the mixing drum and provide first acoustic sensor signaling containing information about when the concrete is lifted by the vane, and sense a second acoustic characteristic when the concrete flows off the vane and falls back into the mixture and provide second acoustic sensor signaling containing information about when the concrete flows off the vane and falls back into the mixture; and the signal processor may be configured to receive the first acoustic sensor signaling and the second acoustic sensor signaling, and determine the corresponding signaling containing information about the slump characteristic of the mixture of concrete contained in the mixing drum, based upon the first acoustic sensor signaling and the second acoustic sensor signaling received.

The signal processor may be configured to determine the slump characteristic based upon a post exit angle of the vane at which the release occurs.

The signal processor may be configured to determine the slump characteristic based upon noise characteristics at different spatial locations that indicate differences in the slump.

The vane of the mixing drum may be mounted on an interior wall of the mixing drum at an interior location, and the acoustic sensor may be mounted on an exterior wall of the mixing drum at an exterior location corresponding to the interior location.

The acoustic sensor may be positioned on the wall and configured to sense the noise of the concrete flowing off a vane of the mixing drum, and provide first acoustic sensor signal containing information about the noise, and sense a dynamic noise of the remixing of the concrete falling back into the mixture, and provide second acoustic sensor signal containing information about the dynamic noise; and the signal processor may be configured to receive the first acoustic sensor signaling and the second acoustic sensor signaling, and determine the corresponding signaling containing information about the slump characteristic of the mixture of concrete contained in the mixing drum, based upon noise characteristics contained in the first acoustic sensor signaling and the second acoustic sensor signaling received.

The signal processor may be configured to determine a high slump mix when the concrete in the mixture is lifted, then pours back off the vane into the mixture at a low post exit angle, and the noise is characterized by a broad band flow noise.

The signal processor may be configured to determine a low slump mix when the concrete in the mixture is lifted, then pours back off the vane into the mixture at a high post exit angle, and the noise is characterized by discrete noise transients.

The post exit angle may be determined by comparing first acoustic sensor signaling containing information about when the concrete is lifted by a scoop sampler of the mixing drum and second acoustic sensor signaling containing information about when the concrete flows off the scoop sampler and falls back into the mixture.

The scoop sampler may be coated with a hydrophobic polymer.

The acoustic sensor may include arrays of SONAR patches configured to sense a differential slurry speed at different locations caused by the motion of drum rotation and provide SONAR patch array signaling containing information about the differential slurry speed at different locations; and the signal processor may be configured to receive the SONAR patch array signaling, and determine the corresponding signaling containing information about the slump characteristic of the mixture of concrete contained in the mixing drum, based upon the SONAR patch array signaling received.

The acoustic sensor may be mounted on an outside wall of the mixing drum.

The acoustic sensor may be mounted on an inside wall of the mixing drum.

The acoustic sensor may include an outside acoustic sensor mounted on an outside wall of the mixing drum, and an inside acoustic sensor mounted on an inside wall of the mixing drum.

The acoustic sensor may include a first SONAR array mounted inside the mixing drum at a first depth and configured to sense a first flow rate of the concrete in the mixture at the first depth, and provide first SONAR array signaling containing information about the first flow rate, and a second SONAR array mounted inside the mixing drum at a second depth that is different than the first depth and configured to sense a second flow rate of the concrete in the mixture at the second depth, and provide second SONAR array signaling containing information about the second flow rate. In addition, the signal processor may be configured to receive the first SONAR array signaling and the second SONAR array signaling, and determine the corresponding signaling containing information about the slump characteristic of the mixture of concrete contained in the mixing drum, based upon the first SONAR array signaling and the second SONAR array signaling received.

The slump characteristic may be based upon a differential flow characteristic sensed and determined.

The acoustic sensor may include a first acoustic-based sensor and a second acoustic-based sensor configured to sense the speed of sound (SoS) in a mixture of concrete contained in a mixing drum in a plurality of different planes/directions. In addition, the system may also include a sensor housing assembly having a mounting wall configured to mount the sensor housing assembly on an interior wall of the mixing drum, a first sensor wall configured to mount the first acoustic-based sensor to sense a first SoS in the mixture of concrete contained in the mixing drum in a first plane/direction of the plurality of different planes/directions, and a second sensor wall configured to mount the second acoustic-based sensor to sense a second SoS in the mixture of concrete contained in the mixing drum in a second plane/direction of the plurality of different planes/directions.

The system may include, or take the form of, a multi-directional speed of sound (SoS) sensor.

The first wall may be configured to face inwardly towards the axis of rotation; and the second wall may be configured to contact the mixture of concrete contained in the mixing drum on a leading edge facing the direction that the mixing drum is rotating.

The second sensor wall may be obliquely-oriented in relation to the mounting wall and the second sensor wall.

The first acoustic-based sensor may be configured to provide first acoustic-based sensor signaling containing information about a first acoustic signaling sensed at a first frequency.

The first acoustic-based sensor may include a first acoustic transmitter configured to provide first acoustic transmitter signaling at the first frequency; and a first acoustic receiver configured to receive the first acoustic transmitter signaling and provide the first acoustic signaling sensed at the first frequency.

The first acoustic transmitter may be configured to be substantially co-planar with the first acoustic receiver on the first sensor wall.

The second acoustic-based sensor may be configured to provide second acoustic-based sensor signaling containing information about a second acoustic signaling sensed at a second frequency.

The second acoustic-based sensor may include a second acoustic transmitter configured to provide second acoustic transmitter signaling at the second frequency; and a second acoustic receiver configured to receive the second acoustic transmitter signaling and provide the second acoustic signaling sensed at the second frequency.

The second acoustic transmitter may be configured to be substantially co-planar with the second acoustic receiver on the second sensor wall.

The first acoustic-based sensor may be configured to provide first acoustic-based sensor signaling containing information about a first acoustic signaling sensed at a first frequency.

The system may include a first SoS processor configured to receive the first acoustic-based sensor signaling and provide first SoS processor signaling containing information about a first entrained air level that depends on a first SoS determination in the mixture of concrete contained in the mixing drum in the first plane/direction; the second acoustic-based sensor is configured to provide second acoustic-based sensor signaling containing information about a second acoustic signaling sensed at a second frequency; and the system comprises a second SoS processor configured to receive the second acoustic-based sensor signaling and provide second SoS processor signaling containing information about a second entrained air level that depends on a second SoS determination in the mixture of concrete contained in the mixing drum in the second plane/direction.

The system may include a slump factor processor configured to receive the first SoS processor signaling and second SoS processor signaling, and provide slump factor processor signaling containing information about a slump factor of the mixture of concrete contained in the mixing drum.

The slump factor processor may be configured to determine the slump factor based upon a difference between the first SoS and the second SoS as a function of the rotation speed of the mixing drum.

The slump factor processor may be configured to receive drum rotation speed signaling containing information about the rotation speed of the mixing drum and determine the slump factor based upon the rotation speed of the mixing drum.

The slump factor processor may be configured to determine a slump response factor ($F_{SR}$) for a rotational speed ($\omega$) by multiplying the difference by a square-root of the first SoS measured based upon the equation:

$$F_{SR}(\omega)=(c_2(\omega)-c_1)*\varphi^{1/2},$$

where $c_2(\omega)$=the second SoS measured at the rotational speed ($\omega$), $c_1$ is the first SoS measured, and $\varphi$ is the Air Void Fraction corresponding to the first entrained air level.

The slump factor processor may be configured to determine the slump response factor ($F_{SR}$) based upon a calibration for various mix recipes and drum rotation speeds to provide an indicator of a real time slump in the mixture of concrete.

The system may include a 3-axis accelerometer configured to respond to angular positions of the sensor housing assembly at given times, and provide angular position signaling containing information about the angular positions of the sensor housing assembly at the given times.

The sensor may be mounted on a hatch door of the rotating container or drum, as well as other parts of the rotating container or drum.

The Signal Processing Functionality

According to some embodiments, the signal processor may be configured to receive signaling containing information about an acoustic characteristic of a mixture of a slurry, including concrete, contained in a mixing drum when rotating and sensed by an acoustic sensor mounted on a wall of the mixing drum, and determine corresponding signaling containing information about a slump characteristic of the mixture of concrete contained in the mixing drum, based upon the signaling received, based upon the signaling received.

BRIEF DESCRIPTION OF THE DRAWING

The drawing includes FIGS. 1a-20, which are not necessarily drawn to scale, as follows:

FIG. 1b is an axial view of one end the acoustic probe shown in FIG. 1a.

FIG. 1c is an axial view of another end the acoustic probe shown in FIG. 1a.

FIG. 4 is a diagram showing an end cross-section of a concrete truck drum having an AIRtrac™ sensor entering and exiting the concrete as the concrete truck drum.

FIG. 5 includes FIGS. 5A and 5B, where FIG. 5A is a diagram showing an end cross-section of a concrete truck drum with concrete having a low viscosity; and where FIG. 5B is a diagram showing the end cross-section of the concrete truck drum with concrete having a high viscosity.

FIG. 20 is a block diagram of a system having a sensor and a signal processor or signal processing module for implementing the present invention.

DETAILED DESCRIPTION OF BEST MODE OF THE INVENTION

Figure 1A:
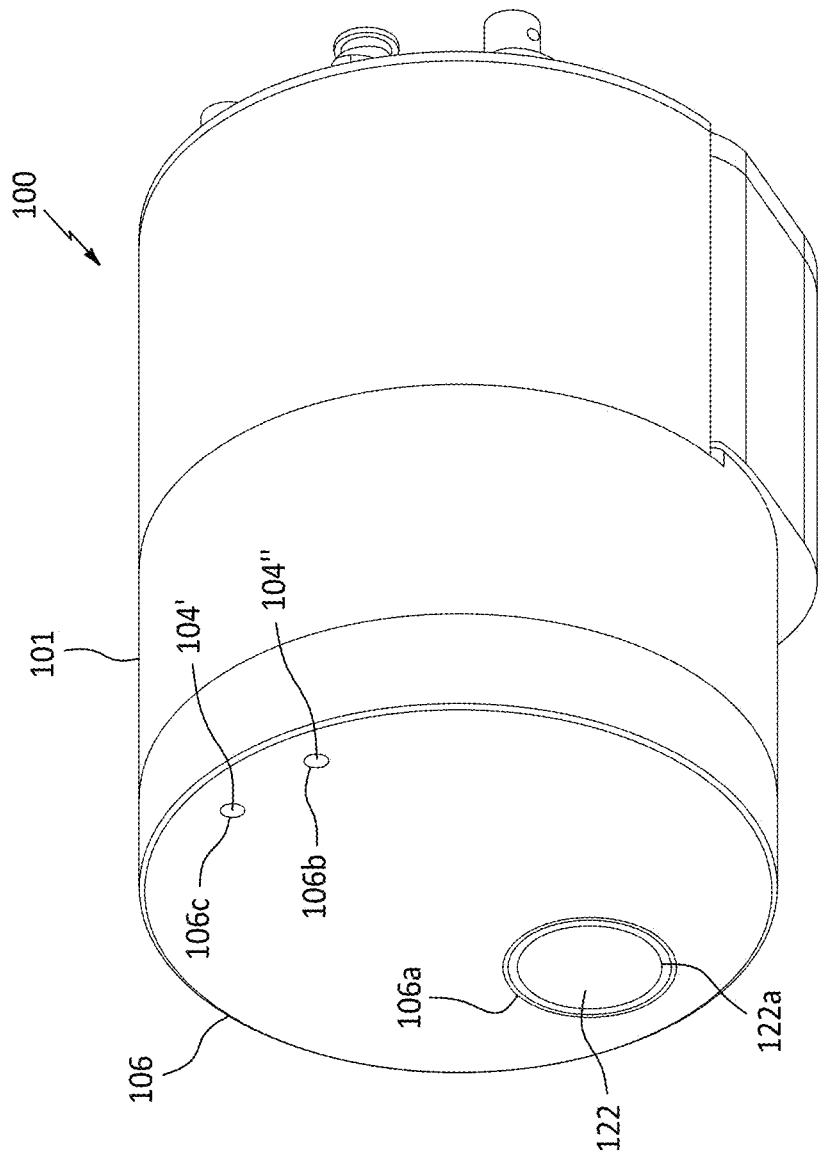
FIG. 1a is a perspective view of an acoustic probe that may be used in some embodiments of the present invention.
Figure 1B:
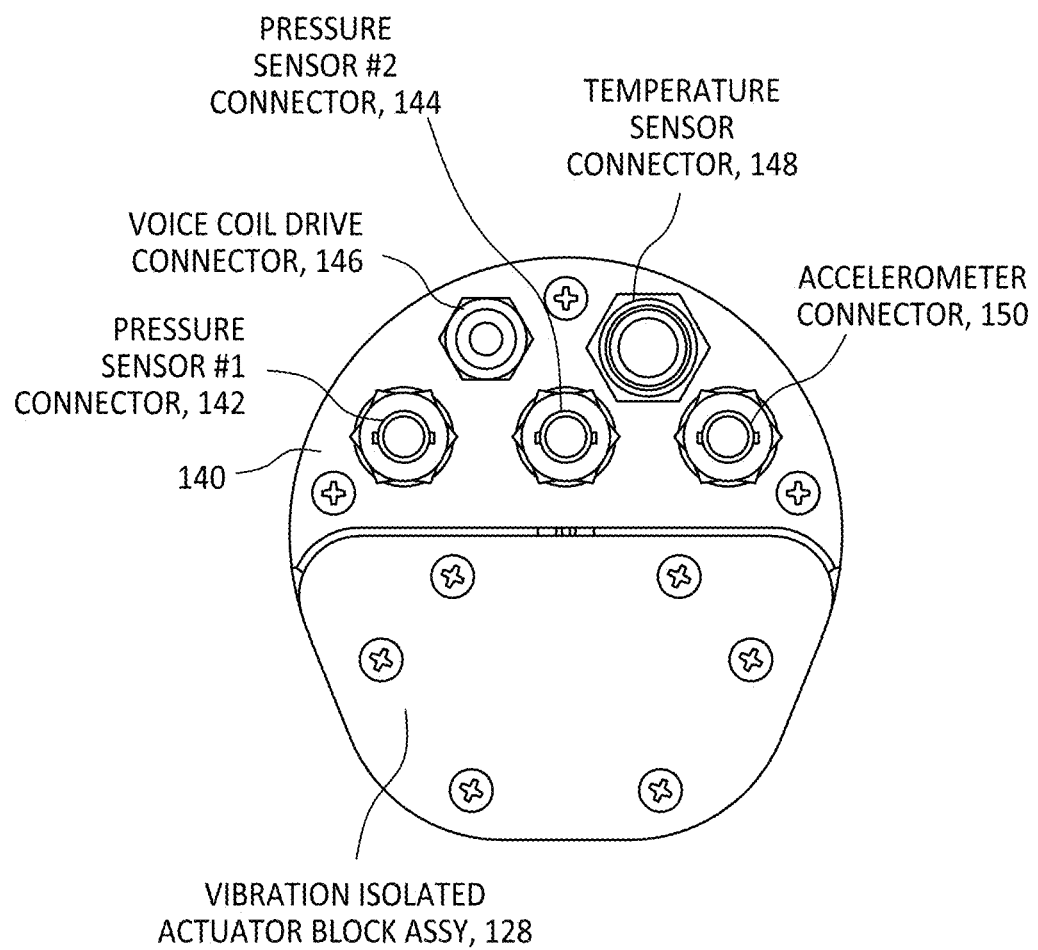
Figure 1C:
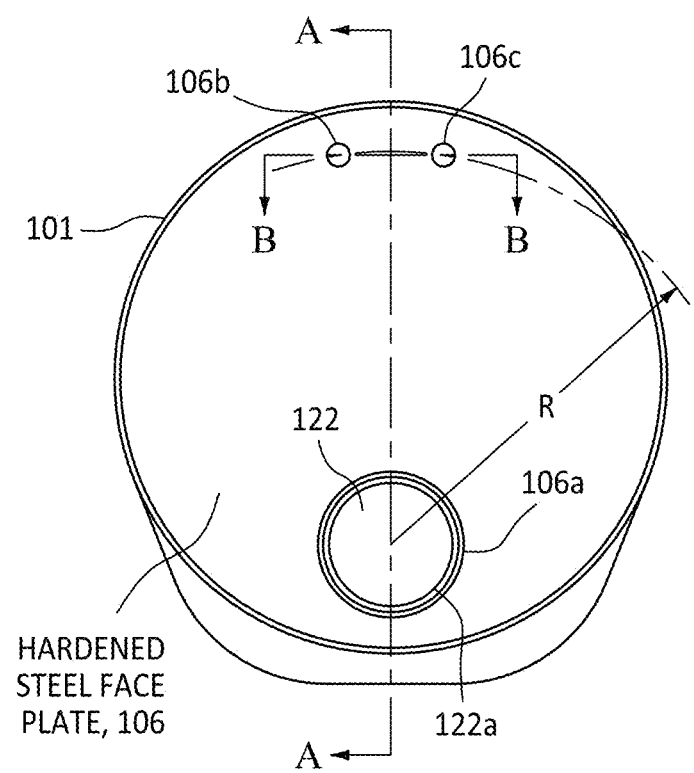
Figure 1D:
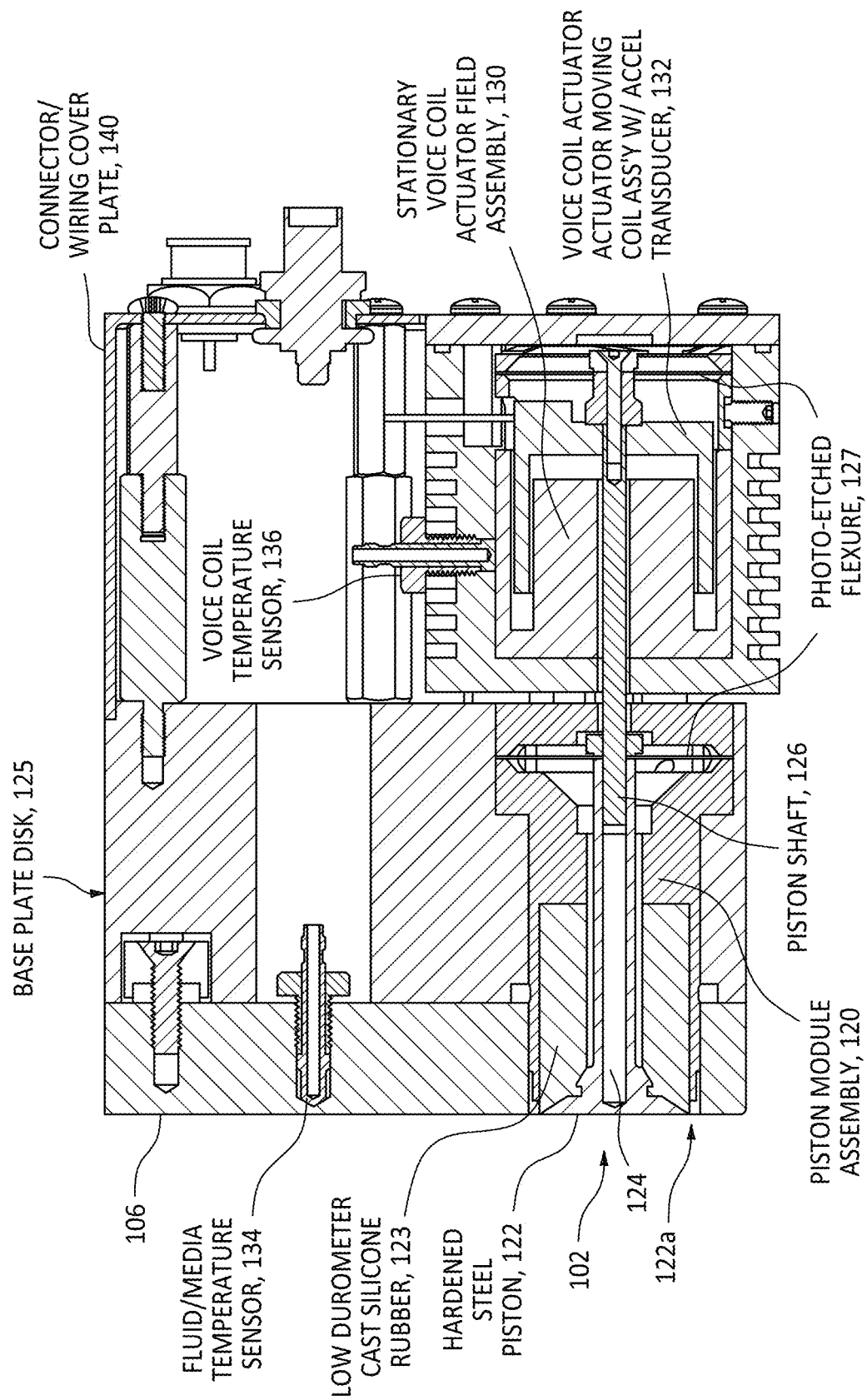
FIG. 1d is a sectional view of the end the acoustic probe shown in FIG. 1c along section lines A-A.
Figure 1E:
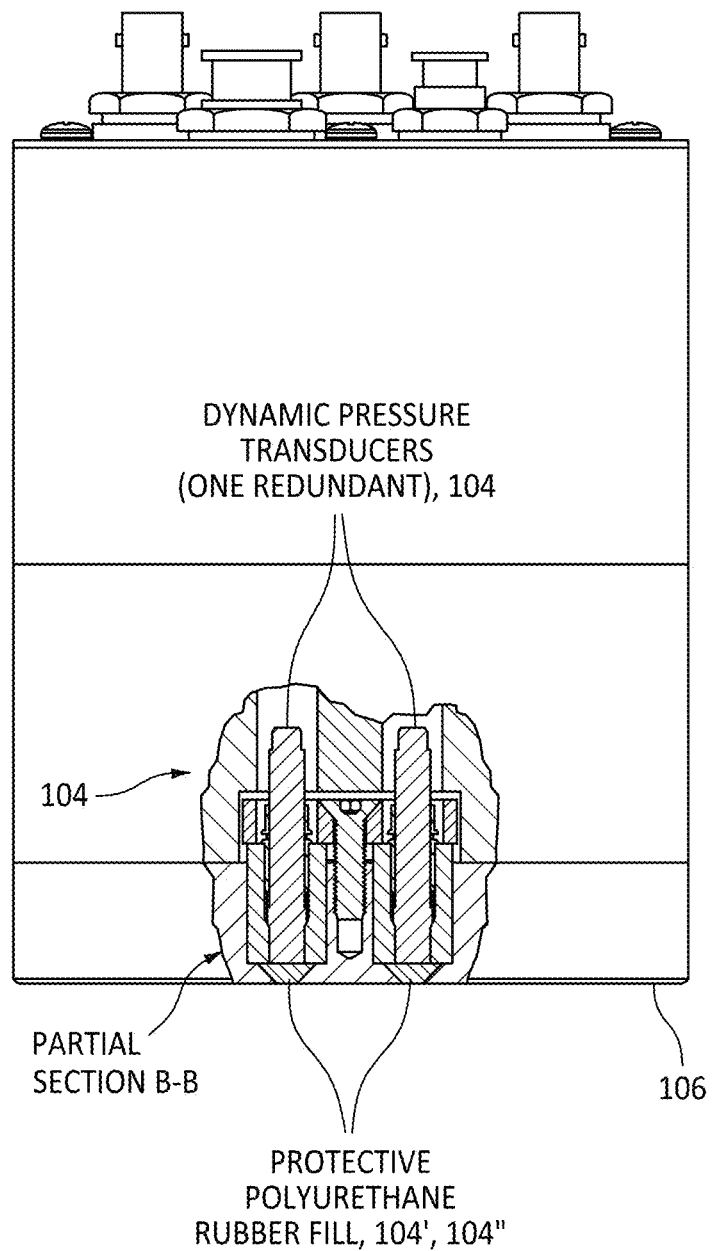
FIG. 1e is a sectional view of the end the acoustic probe shown in FIG. 1c along section lines B-B.
Figure 2:
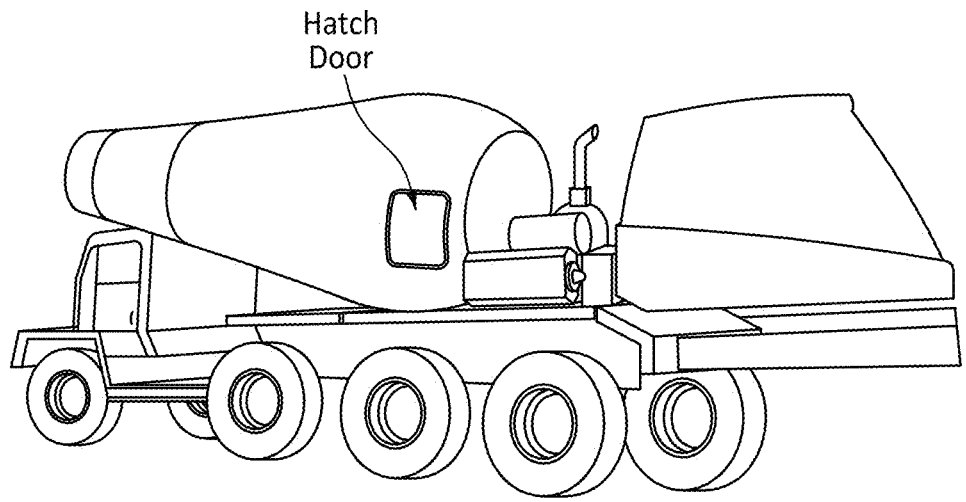
FIG. 2 is a photograph of a ready mix truck with arrow pointing to hatch door indicating potential location of AIRtrac™ sensor installation, which is provided as an example of an AIRtrac™ system installed on a hatch door, and where the hatch door may be located on mixer drum.
Figure 3:
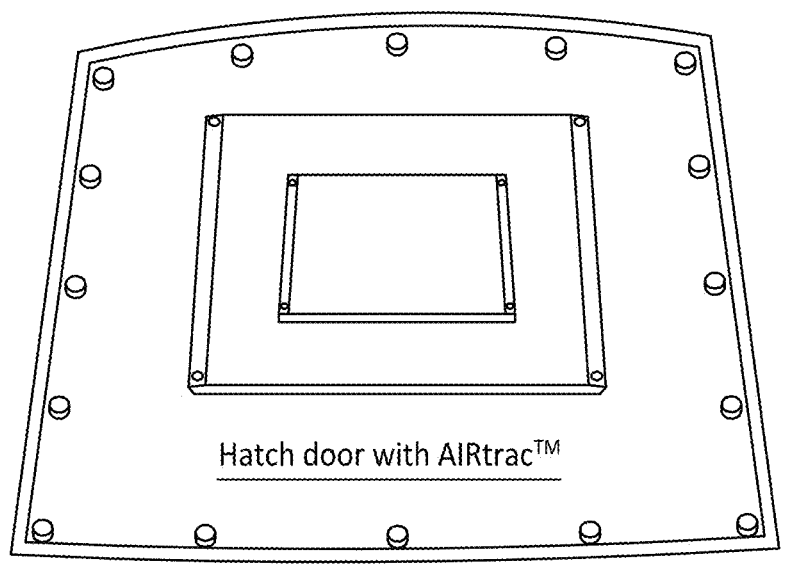
FIG. 3 is a photograph of a hatch door with AIRtrac™ sensor installed.

CCS-0178:: FIGS. 2-5: Techniques for Sensing the Volume and/or Viscosity of Concrete in a Rotating Container or Drum According to some embodiments of the present invention, and consistent with that shown in FIGS. 1a-5, the assignee's AIRtrac™ mobile sensor measures air content by actively creating acoustic waves and measuring the speed of the waves in the concrete media. This is accomplished by using a piston to "pulse" the concrete and measuring the amount of time it takes for the pulse to travel through the concrete and be detected by a pressure transducer that is known distance away from the piston, e.g., consistent with that set forth above. This works very well for the determination of the air content of the concrete mixture but these components can also be used to measure other aspects of the concrete. The present invention sets forth two additional measurements that can be made and used to determine information about the slurry, including concrete.

Volume of Concrete

One parameter that is often not known is the precise volumetric amount of concrete that is in a concrete truck, particularly after a partial pour has occurred. Some measurement techniques known in the art look at the hydraulic loading of the drum, however this is often inaccurate as it requires knowledge of the exact density of the concrete as well as the knowledge of other parameters such as the air content. Using the AIRtrac™ system a much more direct measurement can be made. This measurement technique utilizes the fact that the AIRtrac™ sensor is submerged under the concrete for part of the drums rotation and then is out of the concrete for the remainder. In addition, the AIRtrac™ device has a 3-axis accelerometer that is used to determine the angular position of the sensor at any given time. The combination of knowing the concrete entry and exit angles along with the geometry of the drum, the volume of the concrete can be calculated. FIG. 4 shows a diagram of how this can be achieved.

FIG. 4 shows an approximately half full drum. The AIRtrac™ sensor will enter the concrete at about +90 degrees from vertical and exit at about −90 degrees. This will give an indication that the concrete is occupying about ½ the drum and the volume can be calculated. A simple calculation can be made for other concrete entry/exit angles to yield volume.

The angle of the sensor is always available so the remaining aspect of the measurement is determination of the concrete entry and exit points. Two ways this can be accomplished utilize the pressure transducer. First, a static pressure can indicate when the sensor is under concrete. While in air above the concrete the pressure transducer will show close to 0 pressure, but as the sensor enters the concrete the weight of the concrete will cause a pressure reading. This reading will increase until the sensor is at the bottom of the drum and then decrease until the sensor emerges from the concrete on the other side. Various analysis techniques including least squares curve fitting can be used to extrapolate the exact entry and exit points of the pressure sensor. A second detection technique can utilize the magnitude of the acoustic signal the pressure sensor sees as it is generated by the piston. Air is highly attenuative to acoustic waves so when the AIRtrac™ is in air the pressure transducer will see very little of the acoustic energy generated by the piston, while once the sensor is in the concrete the signal level will rise dramatically. This can also be used to determine when the AIRtrac™ sensor enters and leaves the concrete within the drum.

Viscosity of Concrete

A second parameter of the concrete that the AIRtrac™ can determine is the viscosity of the concrete. The viscosity of a fluid is directly related to the ability of the fluid to flow. Therefore, in a rotating container or drum like a concrete truck a low viscosity fluid will remain very level while a very viscous fluid will tend to not flow very well and will ride up the wall of the drum as the drum exits the fluid. FIG. 5 shows diagrams of the effect.

The amount of the "tilt" of the concrete in the drum will depend on the viscosity of the fluid (or concrete) and the speed of rotation of the drum. The drum rotation speed can be determined by the 3-axis accelerometer and the "tilt" can be determined by the same techniques described above. With knowledge of these parameters along with geometric shape of the drum the concrete viscosity can be determined. Furthermore, with knowledge of the concrete constituents including amount of water, sand, rock and their respective densities, the slump of the concrete can be determined.

CCS-0183:: FIGS. 6-12: Simultaneous Concrete Slump and Air-Content Monitoring Probe Based on Speed of Sound Monitoring for Readymix Delivery Trucks According to some embodiments of the present invention, and consistent with that shown in FIGS. 6-12, the assignee's new AIRtrac™ sensor design can be incorporated internal to a drum mixer to simultaneously determine both the entrained air and slump of the concrete slurry, e.g., based on a determination of the speed of sound (SoS) in the slurry in two, or a plurality of planes—termed here a Multi-Direction SoS—MDSoS—sensor. In particular, see FIG. 6, which illustrates the two axis concept: Here, the AIRtrac™ sensor unit, as described in the aforementioned patent application Ser. No. 14/350,711 (712-2.365-1-1), may be used as the basis of the SoS measurement.

Figure 6:
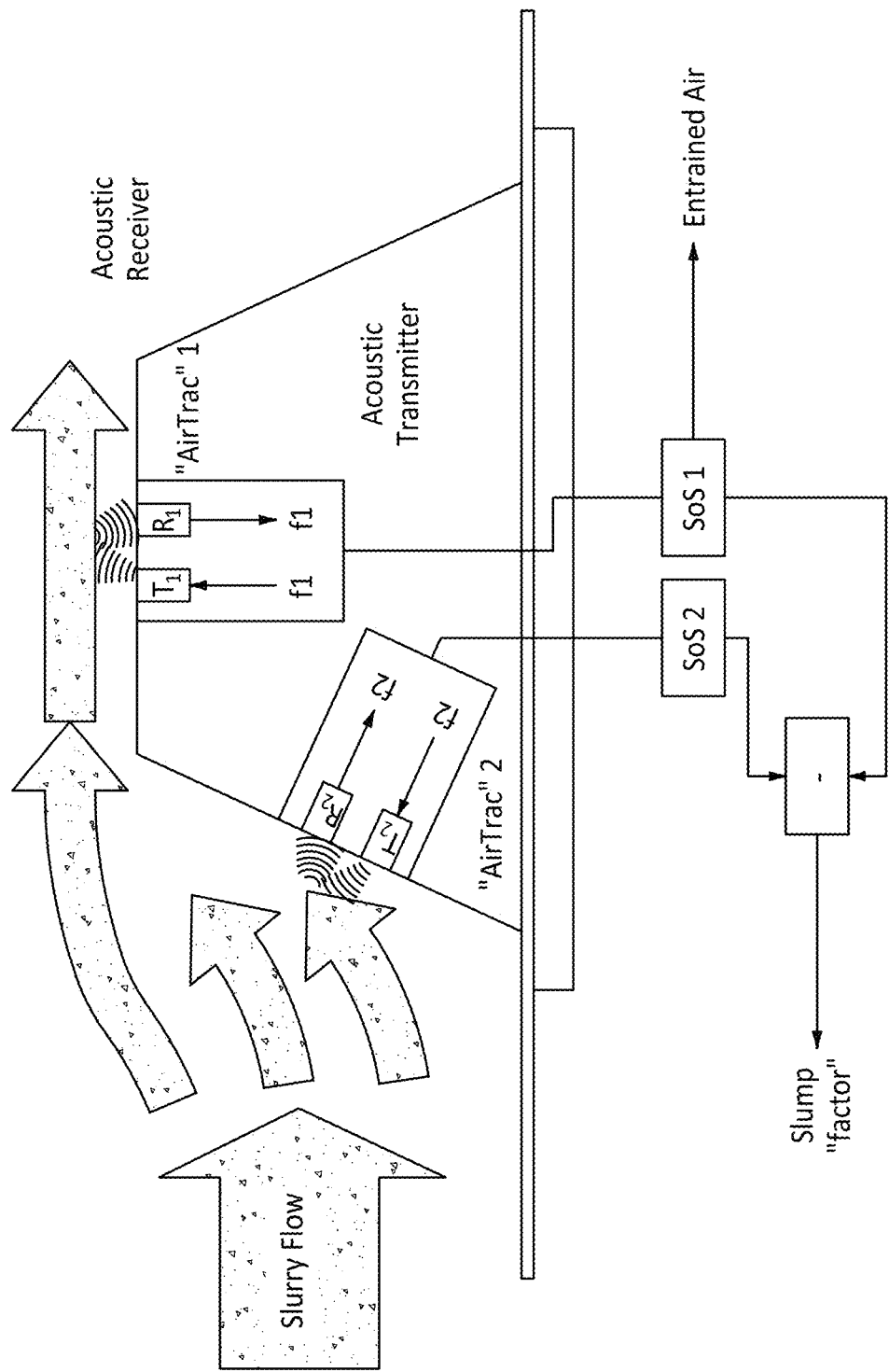
FIG. 6 is a diagram of a sensor system based on monitoring the speed of sound (SoS) in the slurry in a plurality of planes/directions, e.g., using an acoustic based sensor like the assignee's AIRtrac™ sensor.
Figure 7:
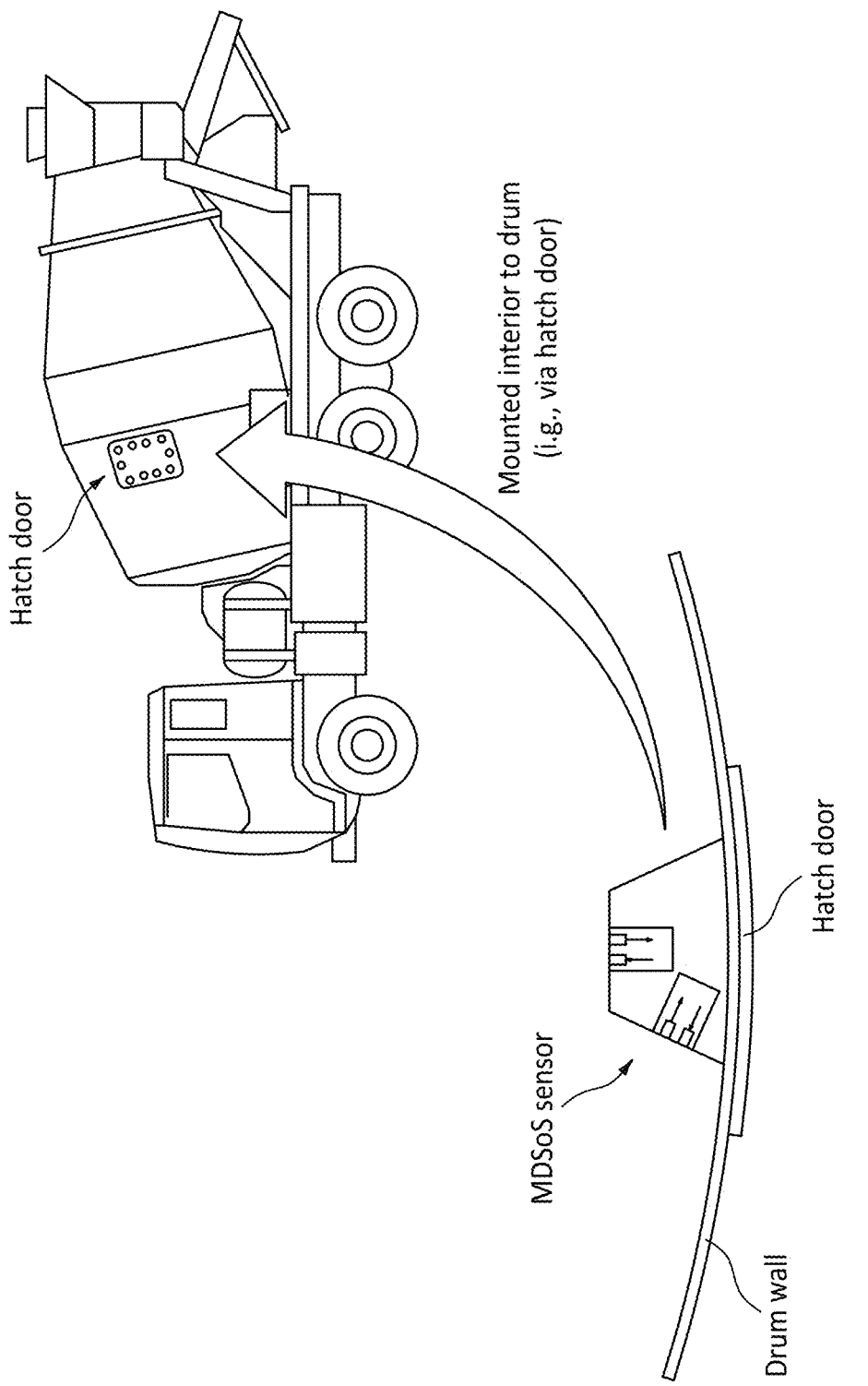
FIG. 7 is a diagram showing the mounting of the multi-directional SoS (MDSoS) sensor on an interior surface of a mixing drum wall.

The device shown in FIG. 6 would be internally integrated into a readymix truck drum, via the drum hatch door, for example, as illustrated in FIG. 7.

The speed of sound in a concrete mix is a function of the entrained air level, and has been used as the basis of a device for such monitoring purposes in concrete mixes (see the reference labeled [9] below). Typically, the device emits a sound signal into the concrete slurry mix at a given frequency, set of frequencies, or is scanned over a range of frequencies. This acoustic signal is then detected at a receiver, or a plurality of receivers (e.g., a microphone or pressure transducer) that are physically offset from the transmitter, and the speed of sound in the slurry assessed.

Figure 8:
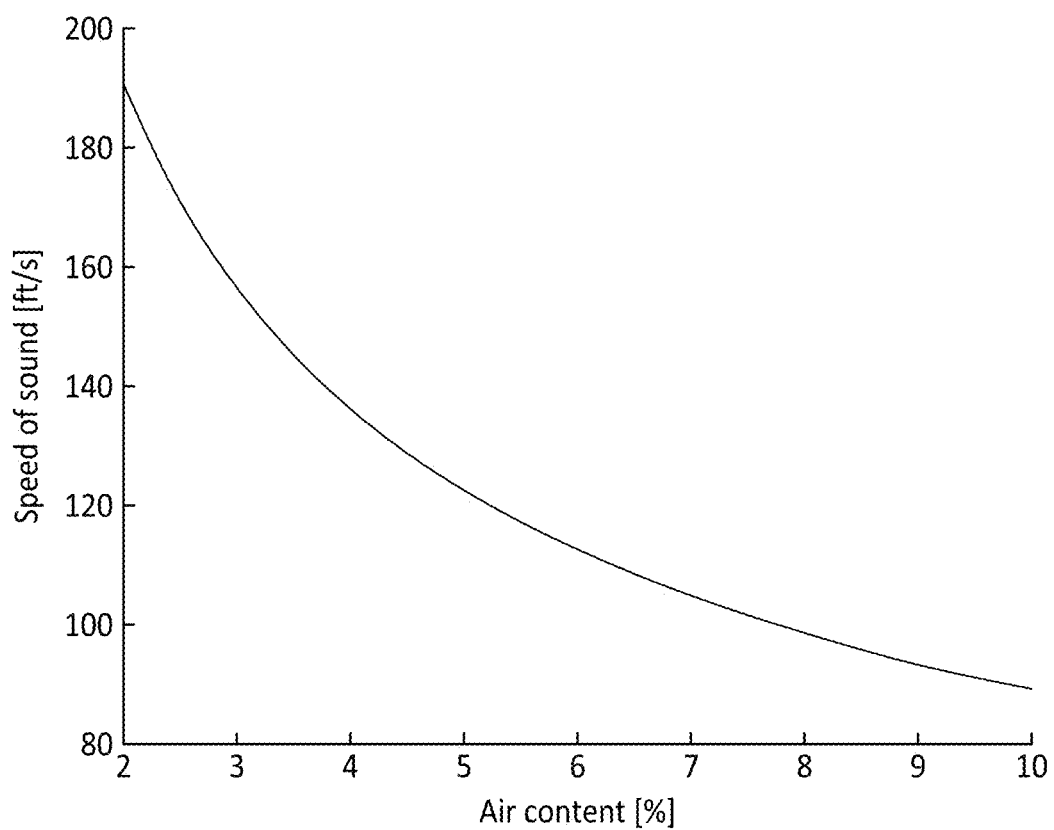
FIG. 8 is a graph of speed of sound (ft/sec) versus air content (%), showing the dependence of the SoS in a concrete mix with entrained air % ($\varphi$).
Figure 9:
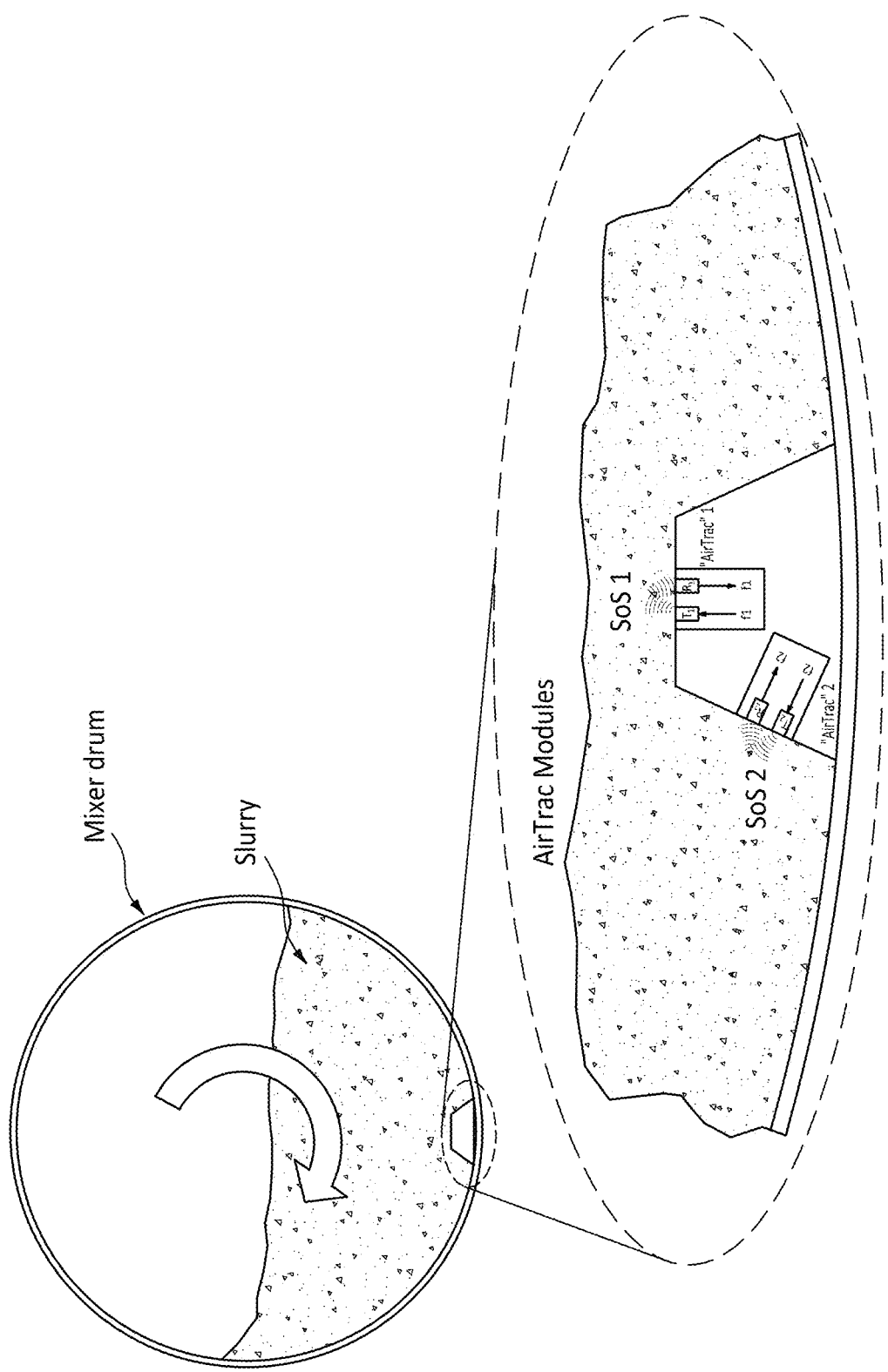
FIG. 9 is a diagram showing the measurement of SoS by two AIRtrac™ sensors/modules at a leading face of a sensor housing and above the sensor housing as it moves through the concrete slurry.

For the relatively low levels of entrained air as typically specified in readymix concrete slurry mixtures, (e.g., less than 10%)—the speed of sound, c, is approximately inversely proportional to the square root of the entrained air level (or Air Void Fraction, $\varphi$), as illustrated in FIG. 8.

In a configuration such as that shown in FIG. 6, with the ready mixer drum loaded with slurry, but stationary, the MDSoS sensor elements (in this case 2 units), labeled as AIRtrac™ #1 and AIRtrac™ #2, will both measure the same SoS in the slurry, e.g., $SoS_1=SoS_2$. However, when the drum rotates (clockwise as shown here), the slurry ahead of the MDSoS sensor housing will undergo compressive forces due to the flow resistance experienced in moving (flowing) around the housing assembly (as depicted by the slurry flow arrows in FIG. 7). These compressive forces will compress the entrained air bubbles in the slurry locally, such that the 'apparent entrained air content' in the slurry immediately ahead of the sensor housing will be lower, and thus the SoS measured higher than that measured by the sensor monitoring the slurry above the sensor housing.

Due to the fact that the slurry will experience lower flow resistance for high slump mixes (high 'workability'), and high resistance for low slump mixes (low 'workability', the compressive forces will be dependent on the slump, or 'workability' of the concrete slurry. Consequently, for a given drum rotation speed, the difference in the SoS monitored for the two AIRtrac™ sensor modules/units will be inversely related to the slump in the concrete. In addition, the compressive forces will be proportional to the drum rotation speed, so this would be required to be monitored to allow for a calibration factor to be attained, which allows the slump factor to be determined at any non-zero rotational speed.

Figure 10:
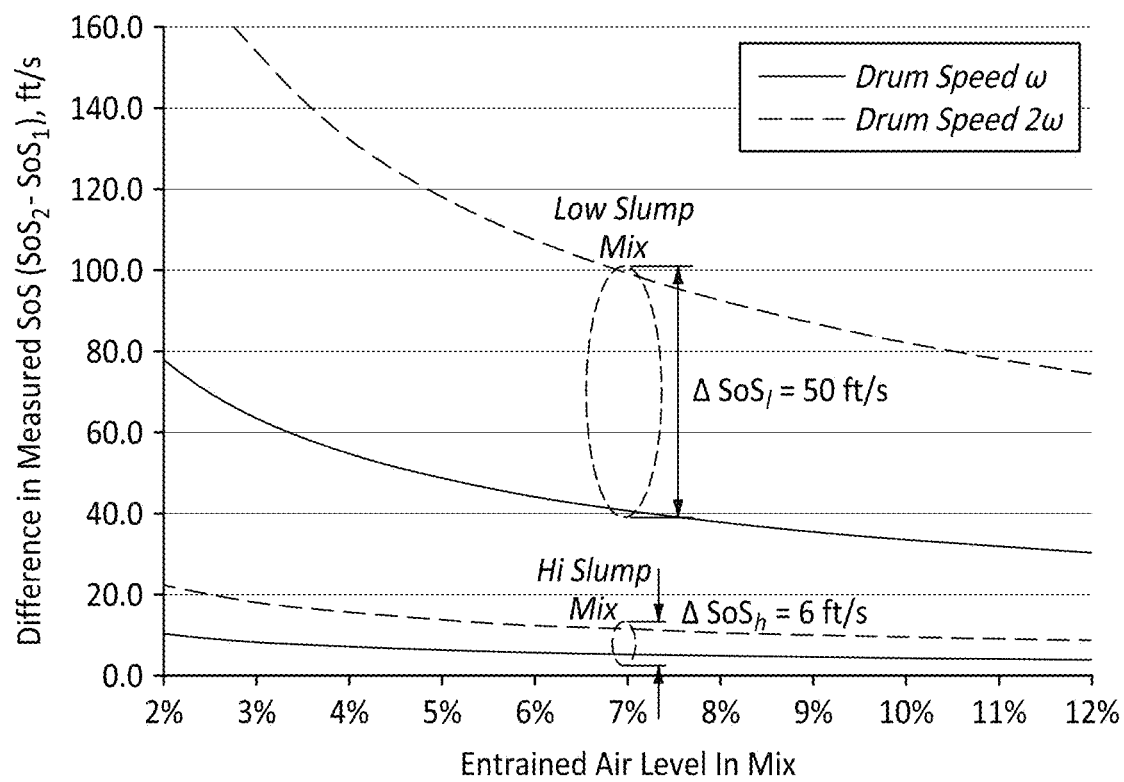
FIG. 10 is a diagram of the difference in the measured SoS ($Sos_2 - S_{oS1}$) in Ft/sec versus entrained air level in mix (%) for two drum speed of w and $2w$, where the difference is measured by two AIRtrac™ sensors/modules ($SoS_2$ measured at the leading face of the sensor housing via AIRtrac™ #2 and $SoS_1$ measured above the sensor housing via AIRtrac™ #1 ($SoS_1$)), and the entrained air content measured via AIRtrac™ #1 ($SoS_1$).

In considering the dependence on the drum speed, it will be realized that the compressional forces due to flow resistance around the sensor housing experienced in the slurry will increase with increased drum rotational speed, thus, higher drum rotational speeds decrease the apparent entrained level in the slurry near the leading edge of the housing, whereas, in principle, the entrained air level measured above the housing will provide the actual entrained air. Consequently, the difference in the SoS measured between the two AIRtrac™ sensor modules will be a function of the drum rotational speed. Therefore, with a given mix slump, the difference in the observed SOS will depend strongly on the drum rotation speed for a low slump mix (stiff mix), whereas for a high slump mix (high workability/low viscosity), the dependence on the drum rotation rate will be low. This dependency is illustrated in FIG. 10 that shows the modelled dependency of the difference in observed SoS at the two AIRtrac™ sensors for a range of different entrained air values, and at a nominal rotational speeds w, and $2w$ (characterized such that at the rotational speed of w, the high slump mix experiences a compression pressure at the leading face of the sensor housing of ~0.1 Bar, and the low slump experiences a compression pressure at the leading face of the sensor housing of ~0.5 Bar). The other parameters—density etc. are typical of the values associated with concrete slurry.

Figure 11:
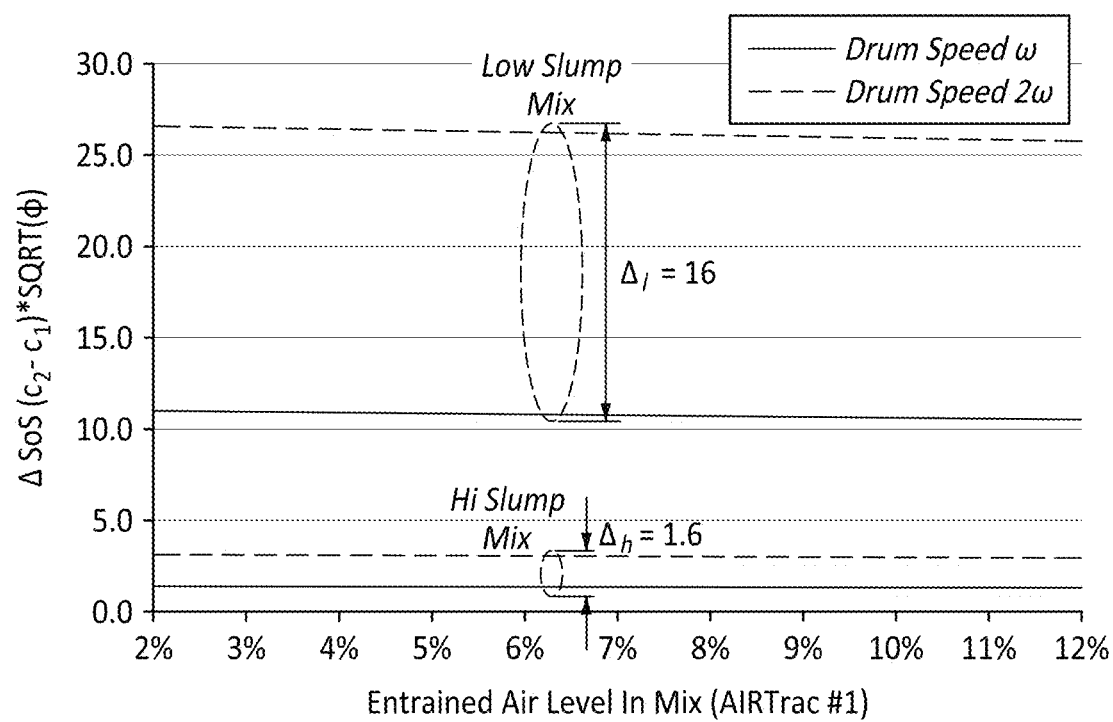
FIG. 11 is a graph of $\Delta SoS(C2-C1)*SQRT(\varphi)$ versus entrained air level in mix (AIRtrac #1) for two drum speed of $\omega$ and $2\omega$, showing the difference in the modelled SoS by the two AIRTrac modules ($SoS_2$ measured at the leading face of the sensor housing via AIRtrac™ #2 and $SoS_1$ measured above the sensor housing via AIRtrac™ #1 ($SoS_1$)) multi-plied by the SQRT of the entrained air in the mix (as measured via AIRtrac #1 ($SoS_1$)) Vs the entrained air in the mix.

The drum rotational speed thus serves as a modulator of the difference in the SoS values. To utilize this approach, a calibration formula or table would need to be created, allowing the slump to be determined from the difference SoS measurements and for various entrained air mixes. Interestingly, however, multiplying the difference in SoS measurements by the square-root of the entrained air level produces a response graph as shown in FIG. 11.

This plot shows a near flat response over the entrained air range of interest in most mix designs (2% to 12%), and produces a slump response factor $F_{SR}$ (where $c_1=SoS_1$, and $c_2=SoS_2$):

$$F_{SR}(\omega)=(c_2(\omega)-c_1)*\varphi^{1/2}$$

Figure 12:
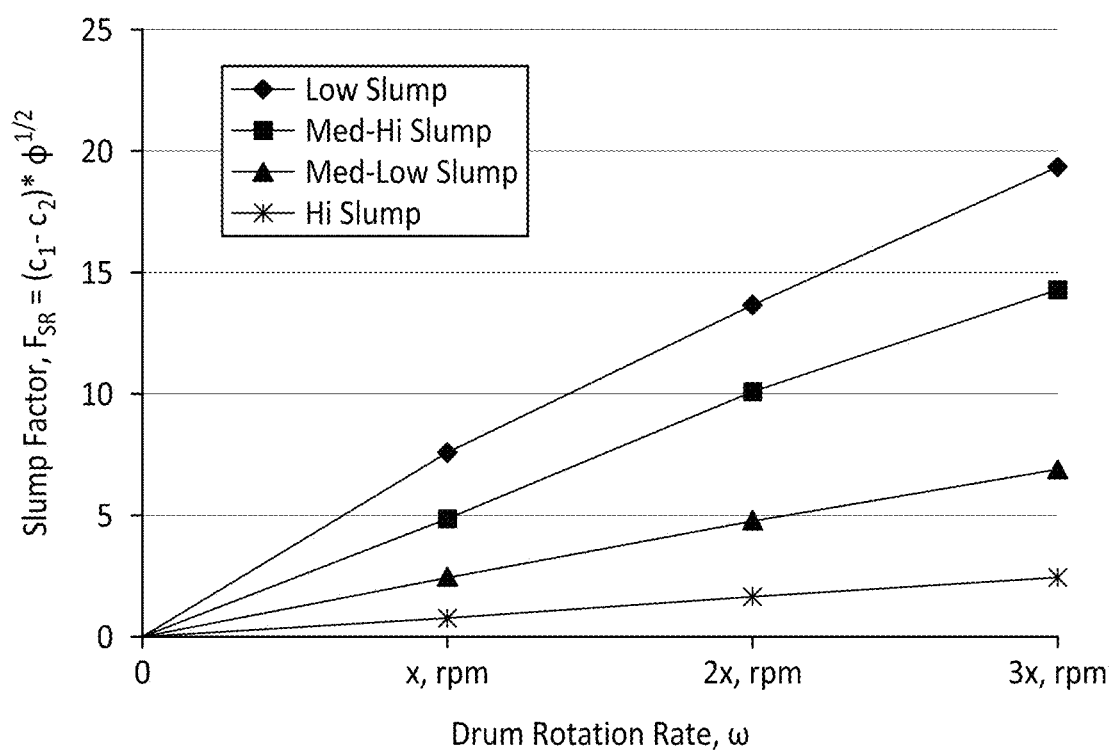
FIG. 12 is a graph of the slump factor ($F_{SR}(\omega)=(c_2(\omega)-c_1)*\varphi^{1/2}$) versus drum rotation rate ($\omega$), showing a modeled dependence of the Slump Response Factor ($F_{SR}$) on the drum rotation rate for 4 different modeled slump mixes, including a low slump, a med-hi slump, a med-low slump and hi slump.

This new factor, is inversely related to the standard slump measurement, but could be calibrated for various mix recipes and drum rotation speeds to provide an indicator of real time slump in the mix. (FIG. 12)

CCS-0185 Acoustic-Based Concrete Slump Monitoring Concept for ReadyMix Trucks

Acoustic Based Slump Monitoring

Figure 14A:
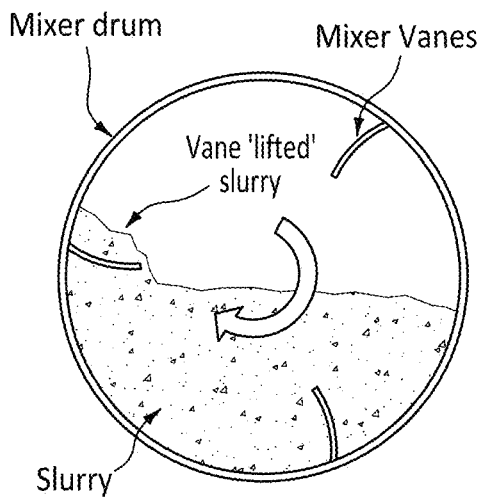
FIG. 14 includes FIGS. 14A and 14B having diagrams showing a mixer drum with mixer vanes configured therein for mixing slurry contained in the mixer drum, e.g., by lifting and releasing the slurry.
Figure 14B:
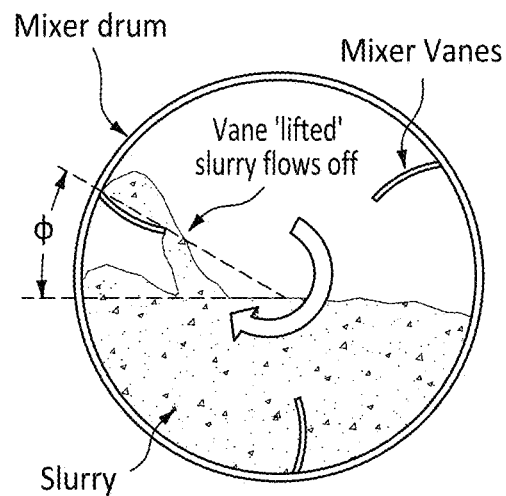
Figure 15:
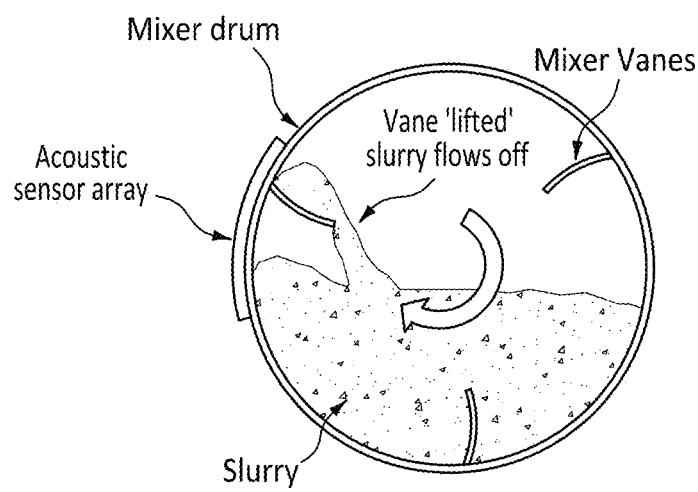
FIG. 15 is a diagram showing a mixer drum having an acoustic sensor array arranged on an outside wall, and having mixer vanes configured therein for mixing slurry contained in the mixer drum, where the acoustic sensor array is positioned to detect the noise of the slurry flowing off the vanes and the dynamic of the remixing.

The mixing of the slurry in a concrete mixer drum is driven by the blades or vanes that create a 'churn' in the slurry, e.g., consistent with that shown in FIGS. 14-16.

The primary purpose of the blades is to lift the slurry (or slurry components initially) as the drum rotates. With each rotation, the lifted slurry drops back into the mixer at the bottom of the drum, creating a mixing dynamic and the cycle repeats again.

Once the slurry components are batched and mixed thoroughly, the dynamics of this mixing process will depend on the slump (workability) of the slurry, e.g.;

For high slump mixes, the slurry will 'flow' smoothly off the blades (vanes), and For low slump mixes, the slurry will tend to fragment into 'clumps' that fall back into the slurry for remixing The noise characteristics generated by the mixing slurry will also thus be slump dependent.

Figure 13:
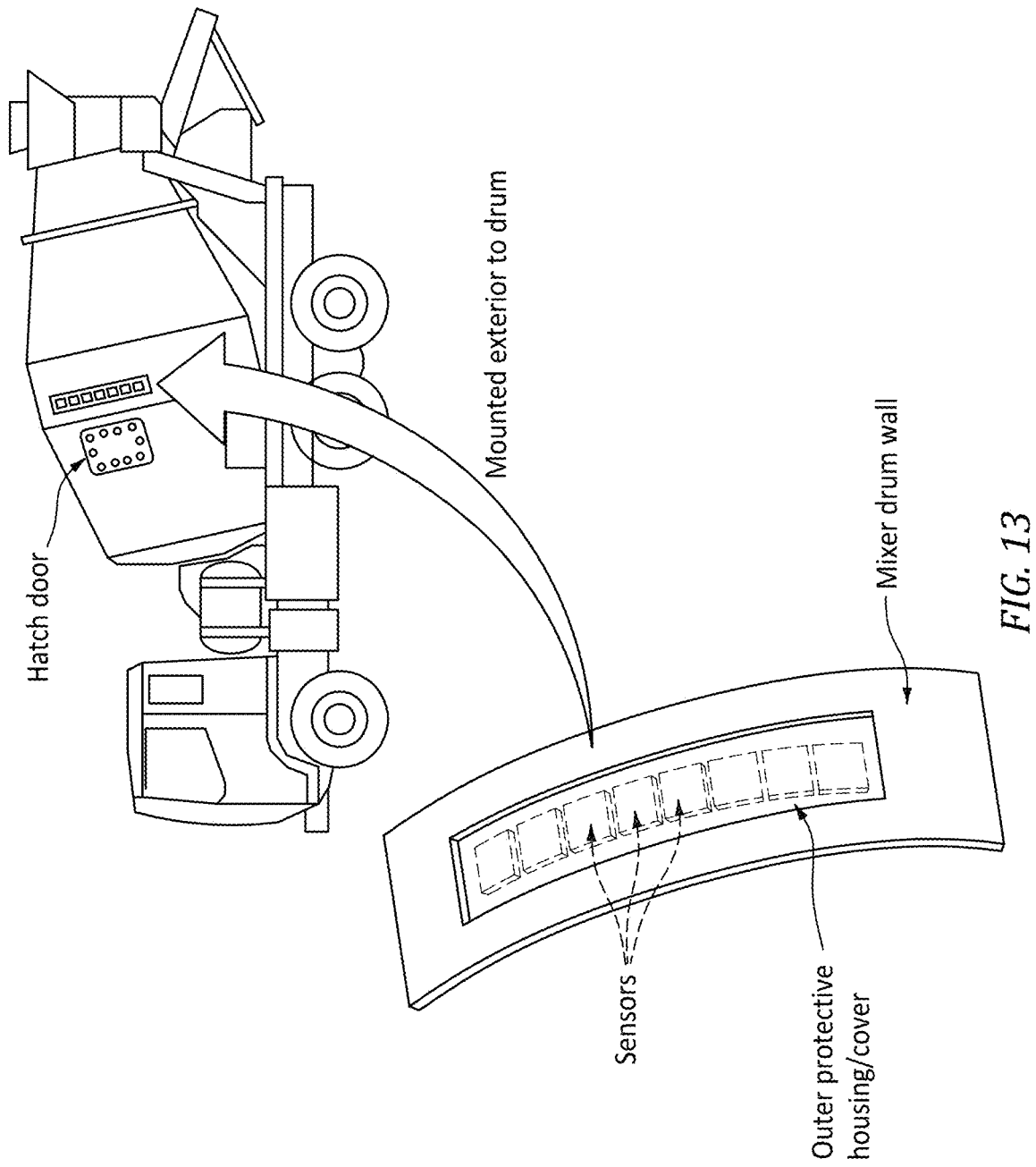
FIG. 13 shows a diagram of a readymix concrete truck having a mixer drum wall with one or more sensors attached thereto.

FIG. 13: Concrete Workability (Slump) Sensor

FIG. 13 shows a readymix concrete truck having a mixer drum wall with one or more sensors attached thereto. By way of example, the sensors may be mounted to the mixer drum wall with a shield housing with good noise isolation characteristics. The sensors may also have an outer protective housing/cover (which may also provide an external noise isolation. Consistent with that shown in FIG. 13, the sensors may include, or take the form of, e.g., PVDF "patches" or PZT elements.

FIG. 14: Flow Over the Vanes

FIG. 14 shows a mixer drum having mixer vanes configured therein for mixing slurry contained in the mixer drum. Consistent with that shown in FIG. 14, the slurry is 'lifted' by the action of the vanes as the drum turns.

The 'lifted' slurry is ultimately released as the drum turns and depending on the slump, it 'flows' off, or 'tumbles' off the vanes and back into the slurry (mixing process).

The slump of the slurry will play a significant role in the dynamics:
1. The 'post exit' angle, $\varphi$, of the vane at which the 'release' occurs, and
2. The noise characteristics created by slurry in the process, e.g., noise characteristics at different spatial locations may indicate differences in the slump of the concrete.

FIG. 15: Acoustic Detection

FIG. 15 shows a mixer drum having mixer vanes configured therein for mixing slurry contained in the mixer drum. The mixer drum also has an acoustic sensor array, e.g., like that shown in FIG. 13.

Consistent with that shown in FIG. 15, the sensor array may be positioned to detect both the noise of the slurry flowing off the vanes, and the dynamics of the 'remixing'.

The slump of the slurry will impact the noise characteristics.

FIG. 16: Slump Impact

Figures 16A, 16B:
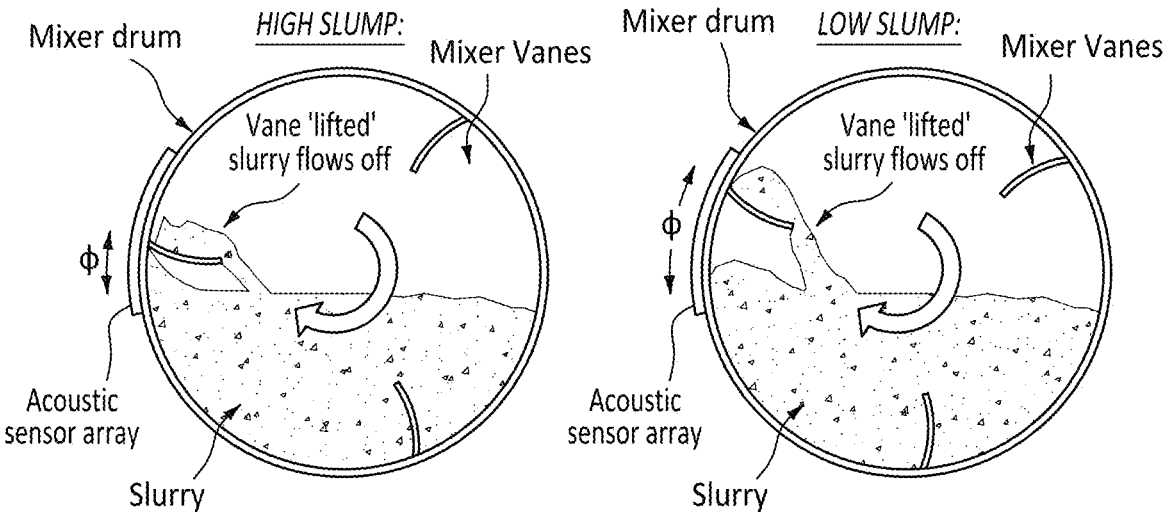
FIG. 16 includes FIGS. 16A and 16B having diagrams with an example of the acoustic impact in relation to high slump and low slump.

FIG. 16 includes FIGS. 16A and 16B, which shows an example of the acoustic impact in relation to high slump and low slump. In operation, the 'churn' effect of the vanes is an important component of the slurry mixing process, but the dynamics are slump-dependent.

FIG. 16A: High Slump

For a high slump mix like that shown in FIG. 16A, the slurry is 'lifted' only slightly then 'pours' back off the vanes into the mix at a low $\varphi$ angle as shown.

The acoustic sensor array will sense noise that is a broader band 'flow' noise.

FIG. 16B: Low Slump

For a low slump mix like that shown in FIG. 16B, the slurry 'lifted' by the action of the vanes fragments and tumbles off the off the vane back into the slurry at a higher φ angle, e.g., when compared to the low φ angle shown in FIG. 16A.

The acoustic sensor array will sense noise that is characterized by more discrete noise transients.

Figure 17:
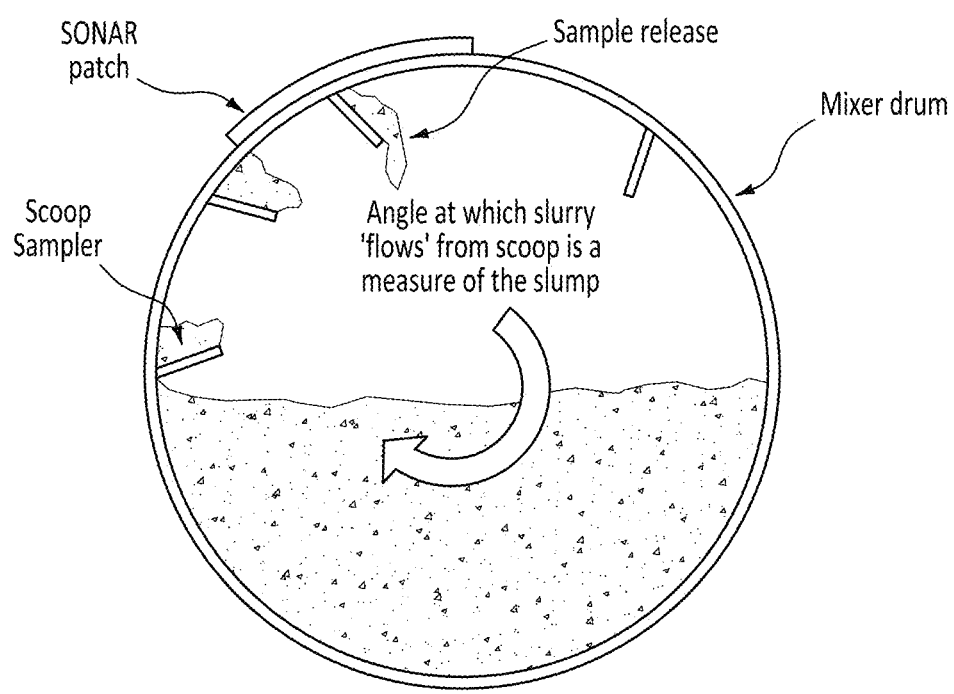
FIG. 17 is a diagram showing a mixer drum having scoop samplers configured on its inside wall and a sensor, e.g., like a SONAR patch, mounted on its outside wall.

FIG. 17: Alternatives: Scoop Sampler

FIG. 17 shows a mixer drum having scoop samplers configured on its inside wall and a sensor, e.g., like a SONAR patch, mounted on its outside wall. In operation, the angle at which the slurry "flows" from the scoop is a measure of the slump of the slurry.

In particular, the scoops' are added to extract a sample of slurry as the drum rotates.

By way of example, the walls of scoop may be coated with a hydrophobic polymer (e.g., like polyurethane (PU)) to allow clean release of sample.

By way of further example, and according to some embodiments, the scoops may include a 'lip' to create the resistance to flow-out.

Consistent with that set forth herein, and according to some embodiments, the mixer drum may be configured to detect the point (i.e., the drum rotation angle) at which the slurry flows out of the scoop sampler.

Consistent with that shown in FIG. 17, the measurement approach may include using a passive acoustic array, e.g., like the SONAR patch shown.

Moreover, the acoustics of this create a frequency or transient type of signature that gives a measure of the concrete slump—use a microphone (or PVDF strip) in AIRtrac™ assembly to monitor.

Figure 18:
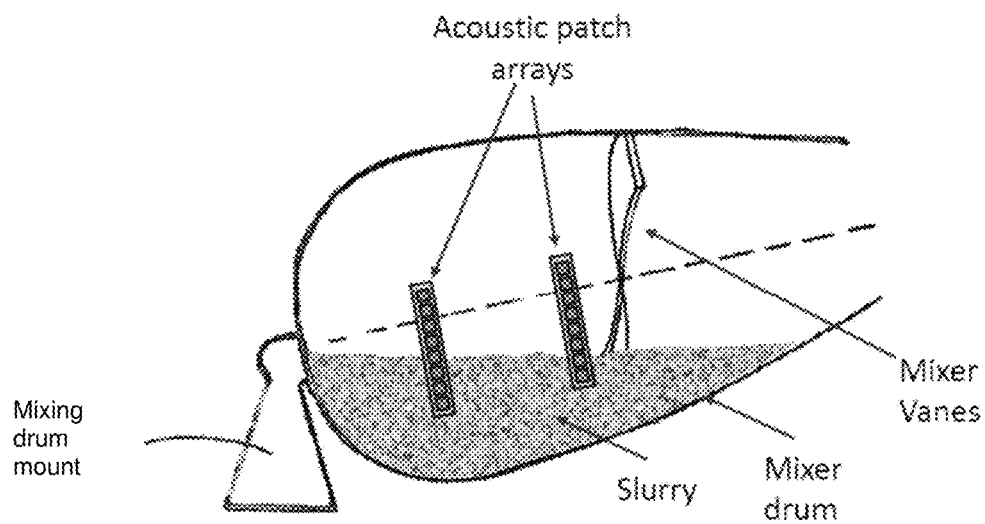
FIG. 18 is a diagram showing a mixer drum having mixer vanes for mixing a slurry contained therein, as well as acoustic patch arrays configured or mounted on the outside wall of the mixer drum.

FIG. 18: Alternatives: Differential Flow

FIG. 18 shows a mixer drum having mixer vanes for mixing a slurry contained therein, as well as acoustic patch arrays configured or mounted on the outside wall of the mixer drum. The mixing drum is mounted on a mixing drum mount as shown.

In operation, the motion of the drum rotation creates an effective differential slurry flow speed at different locations along the drum that could be sensed or picked up by the acoustic patch arrays as shown. By way of example, the acoustic patch arrays may include, or take the form of, SONAR type external patch arrays.

Alternatively, and according to some embodiments, the acoustic patch arrays may be positioned internally under one or more PU layers.

By way of example, and according to some embodiments, characteristics at different 'depths' in the slurry, and different drum RPMs, may also be detected and monitored.

Figure 19:
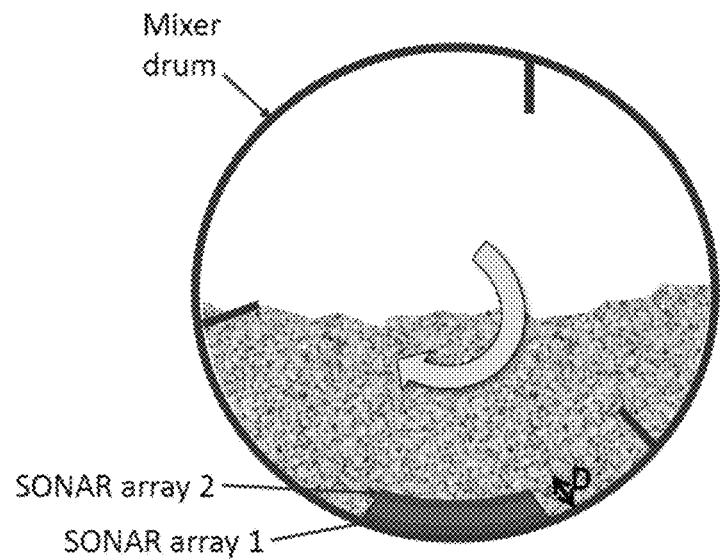
FIG. 19 is a diagram showing a mixer drum having scoops configured therein, as well as two SONAR arrays 1 and 2 configured or mounted on the inside of the mixer drum, e.g., at different depths as shown.

FIG. 19: Alternatives: Differential Flow Sensing

FIG. 19 shows a mixer drum having scoops configured therein, as well as two SONAR arrays 1 and 2 configured or mounted on the inside of the mixer drum, e.g., at different depths as shown. For example, the SONAR array 1 is mounted on the inside wall of the mixer drum at a first depth, while the SONAR array 1 is mounted inside of the mixer drum at a second depth. In effect, the two SONAR arrays 1 and 2 are separated by a standoff depth indicated by an arrow labeled D.

Consistent with that set forth above, the scoops' are added to extract a sample of slurry as the drum rotates.

By way of example, and according to some embodiments, walls of the scoops may be coated with hydrophobic polymer (e.g., like PU) to allow clean release of sample from the scoop.

By way of example, and according to some embodiments, the SONAR array(s) may be used to monitor the slurry flow rate with the drum rotation at the drum surface (e.g., using SONAR array 1), and at one or more standoff depths D into the slurry (e.g., using SONAR array 2).

FIG. 20: The System 10

FIG. 20 shows a system 10 having a sensor (e.g., such as an acoustic-based sensor like element 100, or a PVDF sensor, or a PZT sensor, or a SONAR array sensor) and a signal processor or signal processing module 12 for implementing the present invention.

In operation, the sensor 100, or the PVDF sensor, or the PZT sensor, or the SONAR array sensor may be configured to mount on a wall of a mixing drum like that shown in FIGS. 6, 7, 9 and 13-19, sense an acoustic characteristic of a mixture of a slurry, including concrete, contained in a mixing drum when rotating, and provide acoustic sensor signaling containing information about the acoustic characteristic sensed.

The signal processor 12 may be configured to receive the acoustic sensor signaling, and determine corresponding signaling containing information about a slump characteristic of the mixture of concrete contained in the mixing drum, based upon the signaling received.

The functionality of the signal processor or processor control module 12 may be implemented using hardware, software, firmware, or a combination thereof. In a typical software implementation, the processor module may include one or more microprocessor-based architectures having a microprocessor, a random access memory (RAM), a read only memory (ROM), input/output devices and control, data and address buses connecting the same, e.g., consistent with that shown in FIG. 20, e.g., see element 14. By way of example, the input/output devices may be configured to receive the signaling Sin sensed by the sensor 100, the PVDF sensor, the PZT sensor, and provide the signaling Sin to the signal processor 12 for further processing. By way of further example, the input/output devices may be configured to receive the corresponding signaling $S_{out}$ from the signal processor 12, and provide the corresponding signaling $S_{out}$.

A person skilled in the art would be able to program such a microprocessor-based architecture(s) to perform and implement such signal processing functionality described herein without undue experimentation. The scope of the invention is not intended to be limited to any particular implementation using any such microprocessor-based architecture or technology either now known or later developed in the future.

The Acoustic-Based Sensor

By way of example, the present invention is disclosed based upon using the assignee's AIRtrac™ sensor. However, the scope of the invention is not intended to be limited to the same. For example, embodiments are envisioned, and the scope of the invention is intended to include, e.g. using other types or kinds of acoustic-based sensors either now known or later developed in the future that may be configured to attach inside a rotating container or drum having a known geometry, sense angular positions of the sensor and sense associated entry and exit points when the sensor enters and exits concrete contained in the rotating container or drum, and provide signaling containing information about the angular positions and the associated entry and exit points.

The Rotating Container or Drum

By way of example, the present invention is disclosed based upon using a rotating drum forming part of a concrete mixing truck. However, the scope of the invention is not intended to be limited to the same. For example, embodiments are envisioned, and the scope of the invention is intended to include, e.g. using other types or kinds of rotating containers or drums either now known or later developed in the future that may be configured to receive and contain concrete, as well as rotate and mix the concrete.

The Slurry (e.g., Concrete)

By way of example, the present invention is disclosed based upon mixing a slurry like concrete using a rotating drum. However, the scope of the invention is not intended to be limited to the same. For example, embodiments are envisioned, and the scope of the invention is intended to include, e.g. processing other types or kinds of slurries either now known or later developed in the future, including other types or kinds of slurries that are sensitive to the amount of entrained air contained therein, other types or kinds of or slurries that are mixed and poured from a rotating container or drum.

Means for Attaching

Means for attaching a sensor inside a rotating container or drum is known in the art, and the scope of the invention is not intended to be limited to any particular types or kinds thereof either now known or later developed in the future. By way of example, the sensor may include a sensor housing that may be fastened inside the rotating container or drum using fasteners like screws.

PVDF "Patches" or PZT Elements

PVDF technology including PVDF "patches", as well as PZT technology including PZT elements, are known in the art, and the scope of the invention is not intended to be limited to any particular type or kind thereof either now known or later developed in the future.

Moreover, one skilled in the art would understand and appreciate how to implement PVDF "patches" and/or PZT elements in order to sense noise characteristic, e.g., consistent with that disclosed herein.

REFERENCES

1. U.S. Pat. No. 3,731,909, Johnson
2. U.S. Pat. No. 4,008,093, Kitsuda et al.
3. U.S. Pat. No. 5,713,663, Zandberg and Briedis
4. U.S. Pat. No. 8,020,431, Cooley et al.
5. U.S. Pat. No. 8,858,061, Berman
6. U.S. Pat. No. 9,199,391, Beaupre et al
7. US Patent Publication no. 2009/0171595, Benegas
8. U.S. Pat. No. 6,484,079, Buckelew and Goff
9. Tregger, N., Jeknavorian, A., Loose, D., and Durning, T, Introducing a New Sensor for In-Mixer Air Volume Measurement, Proceedings of 2013 PCI Convention.

THE SCOPE OF THE INVENTION

While the invention has been described with reference to an exemplary embodiment, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A system comprising:
   an acoustic sensor configured to mount on an inside wall of a mixing drum, sense an acoustic characteristic of a mixture of a slurry, including concrete, contained in the mixing drum when rotating, and provide acoustic sensor signaling containing information about the acoustic characteristic sensed; and
   a signal processor configured to
      receive the acoustic sensor signaling, and
      determine corresponding signaling containing information about a slump characteristic of the mixture of the slurry, including concrete, contained in the mixing drum, based upon the acoustic sensor signaling received;
   wherein the acoustic sensor is configured to
      sense a first acoustic characteristic when the concrete is lifted by a vane of the mixing drum and provide first acoustic sensor signaling containing information about when the concrete is lifted by the vane, and
      sense a second acoustic characteristic when the concrete flows off the vane and falls back into the mixture and provide second acoustic sensor signaling containing information about when the concrete flows off the vane and falls back into the mixture; and
   the signal processor is configured to
      receive the first acoustic sensor signaling and the second acoustic sensor signaling, and
      determine the corresponding signaling containing information about the slump characteristic of the mixture of concrete contained in the mixing drum, based upon the first acoustic sensor signaling and the second acoustic sensor signaling received.

2. The system according to claim 1, wherein the signal processor is configured to determine the slump characteristic based upon noise characteristics at different spatial locations that indicate differences in the slump.

3. The system comprising:
   an acoustic sensor configured to mount on an inside wall of a mixing drum, sense an acoustic characteristic of a mixture of a slurry, including concrete, contained in the mixing drum when rotating, and provide acoustic sensor signaling containing information about the acoustic characteristic sensed; and
   a signal processor configured to
      receive the acoustic sensor signaling, and
      determine corresponding signaling containing information about a slump characteristic of the mixture of the slurry, including concrete, contained in the mixing drum, based upon the acoustic sensor signaling received;
   wherein the acoustic sensor is positioned on the inside wall and configured to
      sense the noise of the concrete flowing off a vane of the mixing drum, and provide first acoustic sensor signal containing information about the noise, and sense a dynamic noise of the remixing of the concrete falling back into the mixture, and provide second acoustic sensor signal containing information about the dynamic noise; and the signal processor is configured to
receive the first acoustic sensor signaling and the second acoustic sensor signaling, and
determine the corresponding signaling containing information about the slump characteristic of the mixture of concrete contained in the mixing drum, based upon noise characteristics contained in the first acoustic sensor signaling and the second acoustic sensor signaling received.

4. A system comprising:
a signal processor configured to
receive signaling containing information about an acoustic characteristic of a mixture of a slurry, including concrete, contained in a mixing drum when rotating and sensed by an acoustic sensor mounted on an inside wall of the mixing drum, the signaling includes first acoustic sensor signaling containing information about a first acoustic characteristic when the concrete is lifted by a vane of the mixing drum, and second acoustic sensor signaling containing information about a second acoustic characteristic when the concrete flows off the vane and falls back into the mixture; and determine corresponding signaling containing information about a slump characteristic of the mixture of concrete contained in the mixing drum, based upon the first acoustic sensor signaling and the second acoustic sensor signaling received.

5. A system comprising:
a signal processor configured to
receive signaling containing information about an acoustic characteristic of a mixture of a slurry, including concrete, contained in a mixing drum when rotating and sensed by an acoustic sensor mounted and positioned on an inside wall of the mixing drum, the signaling includes first acoustic sensor signaling containing information about the noise of the concrete flowing off a vane of the mixing drum, and second acoustic sensor signaling containing information about a dynamic noise of the remixing of the concrete falling back into the mixture; and
determine corresponding signaling containing information about a slump characteristic of the mixture of concrete contained in the mixing drum, based upon the signaling received, based upon noise characteristics contained in the first acoustic sensor signaling and the second acoustic sensor signaling received.

* * * * *